(12) United States Patent
Karciauskas et al.

(10) Patent No.: US 12,201,516 B2
(45) Date of Patent: Jan. 21, 2025

(54) ELECTROSPUN MEDICAL DEVICES AND METHODS OF MAKING ELECTROSPUN MEDICAL DEVICES

(71) Applicant: Medtronic, Inc., Minneapolis, MN (US)

(72) Inventors: Evaldas Karciauskas, Santa Rosa, CA (US); Salvador Avelar, Santa Rosa, CA (US); Todd Grodrian, Santa Rosa, CA (US); Mike Krivoruchko, Forestville, CA (US); Mingfei Chen, Santa Rosa, CA (US); Christopher Storment, Sonoma, CA (US); David A. Shumaker, Eureka, MT (US); Mark M. Wegner, Kensington, CA (US); Joseph A. Traina, Napa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 979 days.

(21) Appl. No.: 16/519,738

(22) Filed: Jul. 23, 2019

(65) Prior Publication Data

US 2020/0022807 A1 Jan. 23, 2020

Related U.S. Application Data

(60) Provisional application No. 62/702,122, filed on Jul. 23, 2018.

(51) Int. Cl.
*D04H 1/728* (2012.01)
*A61F 2/24* (2006.01)
(Continued)

(52) U.S. Cl.
CPC .......... *A61F 2/2415* (2013.01); *A61F 2/2418* (2013.01); *B29C 33/34* (2013.01);
(Continued)

(58) Field of Classification Search
CPC .................................................... D04H 1/728
See application file for complete search history.

(56) References Cited

U.S. PATENT DOCUMENTS

2002/0090725 A1   7/2002   Simpson et al.
2006/0253192 A1   11/2006  Atala et al.
(Continued)

FOREIGN PATENT DOCUMENTS

| CN | 101690683 | 4/2010 |
| CN | 106999279 | 8/2017 |
| WO | 2016073189 | 5/2016 |

OTHER PUBLICATIONS

The Search Report and Written Opinion for International Application No. PCT/US2019/043025 mailed Oct. 11, 2019 (13 pgs.).

*Primary Examiner* — Seyed Masoud Malekzadeh
*Assistant Examiner* — Tiffany Yu Huang
(74) *Attorney, Agent, or Firm* — Wentsler LLC

(57) ABSTRACT

A method of forming an electrospun prosthetic valve includes utilizing a rotatable and angularly adjustable prosthetic valve mold. The prosthetic valve mold is set to a first angle. The prosthetic valve mold is rotated at a first rotational velocity and a first layer of electrospun fibers is deposited on the prosthetic valve mold. The prosthetic valve mold is stopped and a frame is positioned over the first layer. The prosthetic valve mold is set to a second angle. The prosthetic valve mold is rotated at a second velocity and a second layer of electrospun fibers is deposited on an outer surface of the first layer and an outer surface of the frame.

13 Claims, 26 Drawing Sheets

(51) Int. Cl.
*B29C 33/34* (2006.01)
*B29C 33/38* (2006.01)
*B29C 33/42* (2006.01)
*B29C 35/02* (2006.01)
*B29C 35/16* (2006.01)
*B29C 37/00* (2006.01)
*D01D 5/00* (2006.01)
*A61L 27/34* (2006.01)

(52) U.S. Cl.
CPC .............. *B29C 33/38* (2013.01); *B29C 33/42* (2013.01); *B29C 35/02* (2013.01); *B29C 35/16* (2013.01); *B29C 37/0053* (2013.01); *D01D 5/0007* (2013.01); *D01D 5/0076* (2013.01); *A61F 2/246* (2013.01); *A61F 2/2466* (2013.01); *A61L 27/34* (2013.01); *A61L 2430/20* (2013.01)

(56) References Cited

U.S. PATENT DOCUMENTS

| | | |
|---|---|---|
| 2008/0038352 A1 | 2/2008 | Simpson et al. |
| 2008/0131965 A1 | 6/2008 | Baaijens |
| 2010/0233115 A1* | 9/2010 | Patel ..................... A61L 15/26 425/174.8 E |
| 2012/0295021 A1* | 11/2012 | Peno ..................... B29C 48/04 118/308 |
| 2014/0058498 A1* | 2/2014 | Hannes ................... D01F 6/70 623/1.13 |
| 2016/0047063 A1* | 2/2016 | Khandaker .......... D01D 5/0069 425/174.8 E |
| 2017/0135796 A1* | 5/2017 | Sostek ..................... A61F 2/07 |
| 2017/0340460 A1* | 11/2017 | Rosen ..................... A61F 2/07 |
| 2018/0071088 A1 | 3/2018 | Badhwar et al. |

\* cited by examiner

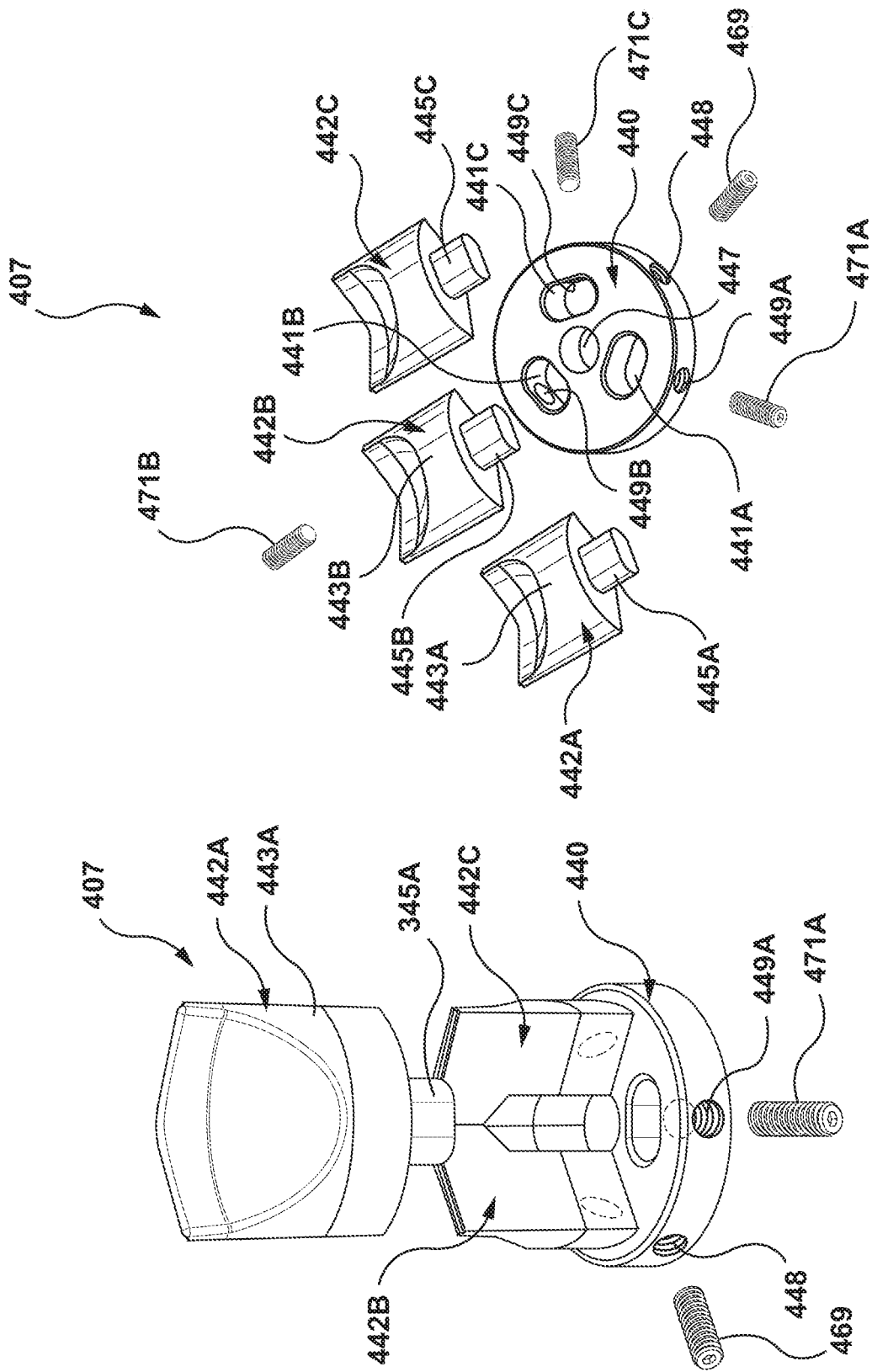

ELECTROSPUN MEDICAL DEVICES AND METHODS OF MAKING ELECTROSPUN MEDICAL DEVICES

RELATED APPLICATIONS

This Non-Provisional Patent Application claims the benefit of the filing date of U.S. Provisional Patent Application Serial No. 62/702,122, filed Jul. 23, 2018, entitled "Electrospun Medical Devices and Methods of Making Electrospun Medical Devices," which is herein incorporated by reference.

BACKGROUND

A wide range of medical treatments exist that utilize medical devices such as prosthetic valves. As used herein, the term "prosthetic valve" is intended to cover medical devices that are adapted to replace a diseased or damaged bodily valve such as, without limitation, a heart valve including an aortic valve, a mitral valve, a pulmonary valve and a tricuspid valve. These prosthetic valves often include a stent-like frame, also referred to as a stent frame, a stent, or a frame. The prosthetic valve is received within the stent-like frame and is coupled thereto. The stent-like frame provides structural support to the prosthetic valve and permits anchoring of the prosthetic valve when deployed in situ at the site of a damaged or diseased native valve. Further, the stent-like frame permits the prosthetic valve to be crimped or radially compressed for delivery via a transcatheter delivery system. As used herein, the terms "stent-like frame", "stent frame", "stent", and "frame" are intended to cover medical devices that are adapted for temporary or permanent implantation within a body lumen, such as without limitation, native heart valves, arteries, and veins.

Prosthetic valves have been made by a variety of methods, including using animal tissue (i.e. a bovine or porcine valve). The animal tissue is sewn or sutured to a frame by hand in a tedious and time-consuming process. In such a process, most of the animal tissue is discarded and wasted. Accordingly, such methods can be laborious, expensive, and time-consuming.

It would therefore be desirable to manufacture a medical device such as a prosthetic valve from a biocompatible artificial material to improve yields, to reduce costs, and to reduce manufacturing time.

SUMMARY

Embodiments hereof relate to a method of making an electrospun prosthetic valve using an electrospinning process. A prosthetic valve mold is set at a first angle. The prosthetic valve mold is rotated at a first rotational velocity, and a first layer of a first plurality of electrospun fibers is deposited on to an outer surface of the prosthetic valve mold. When the first layer has been deposited on to the prosthetic valve mold, rotation of the prosthetic valve mold is stopped. A frame is positioned over or radially outward of the first layer. When the frame is positioned radially outward of the first layer, the prosthetic valve mold is set to a second angle and then rotated at a second rotational velocity. A second layer of a second plurality of electrospun fibers is deposited on an outer surface of the rotating frame and an outer surface of the first layer. When the second layer has been deposited on the outer surface of the frame and the outer surface of the first layer, rotation of the prosthetic valve mold is stopped. The electrospun prosthetic valve is removed from the prosthetic valve mold. The prosthetic valve mold may then be further processed.

Embodiments hereof also relate to an electrospun prosthetic valve having a radially expanded configuration, a radially compressed configuration, and a lumen extending from an inflow end to an outflow end. The electrospun prosthetic valve further includes a first layer. The first layer is formed of a first plurality of electrospun fibers and includes a plurality of leaflets configured to permit flow in one direction to regulate flow through the lumen of the electrospun prosthetic valve. The first layer is formed in an electrospinning process on a rotatable and angularly adjustable prosthetic valve mold.

Embodiments hereof further relate to a system for forming an electrospun prosthetic valve. The system includes a collection assembly and an electrospinning assembly. The collection assembly includes a rotatable and angularly adjustable prosthetic valve mold. The electrospinning assembly is configured to deposit a plurality of electrospun fibers onto the prosthetic valve mold to form the electrospun prosthetic valve.

BRIEF DESCRIPTION OF DRAWINGS

The foregoing and other features and advantages of disclosed embodiments will be apparent from the following description of embodiments hereof as illustrated in the accompanying drawings. The accompanying drawings, which are incorporated herein and form a part of the specification, further serve to explain the principles of the disclosure and to enable a person skilled in the pertinent art to make and use the disclosed embodiments. The drawings are not to scale.

FIG. 3A depicts a perspective illustration of a prosthetic valve mold with separable parts according to an embodiment hereof.

FIG. 3B shows the parts of the prosthetic valve mold of FIG. 3A.

DETAILED DESCRIPTION

Specific embodiments of the present disclosure are now described with reference to the figures, wherein like reference numbers indicate identical or functionally similar elements.

The following detailed description is merely exemplary in nature and is not intended to limit the present technology or the application and uses of the present technology. Although the description of embodiments hereof is in the context of prosthetic valves, the present technology may also be used in other devices. Furthermore, there is no intention to be bound by any expressed or implied theory presented in the preceding technical field, background, brief summary or the following detailed description.

In embodiments hereof, methods are described to manufacture medical devices, such as prosthetic valves, from electrospun fibers in an electrospinning process. The use of the electrospun fibers in the manufacturing of the described prosthetic valves reduces or eliminates the costly and time consuming use of animal tissue in the production of many current prosthetic valves. More specifically, with current animal tissue designs, most of the animal tissue is wasted during the manufacturing process. Further, manufacturing of prosthetic valves with animal tissue is tedious, requiring technicians to manually suture the animal tissue onto biocompatible structures, such as stent-like frames. As a result, current methods of manufacturing animal tissue design prosthetic valves are expensive and time consuming. Further, the manual or hand suturing produces lower than desired yields. The methods and prosthetic valves described herein according to embodiments hereof utilized one or more layers of electrospun fibers that reduces waste as the electrospun fibers are deposited on a valve mold in the desired shape of the valve. Further, in some embodiments, suturing is not required. Further, the use of the electrospun fibers and the electrospinning process in the manufacturing of the electrospun prosthetic valves permits more precise control of the material properties of the electrospun prosthetic valves. Accordingly, the methods described herein result in reduced manufacturing costs, reduced manufacturing time, and improved manufacturing yields.

Figure 1:
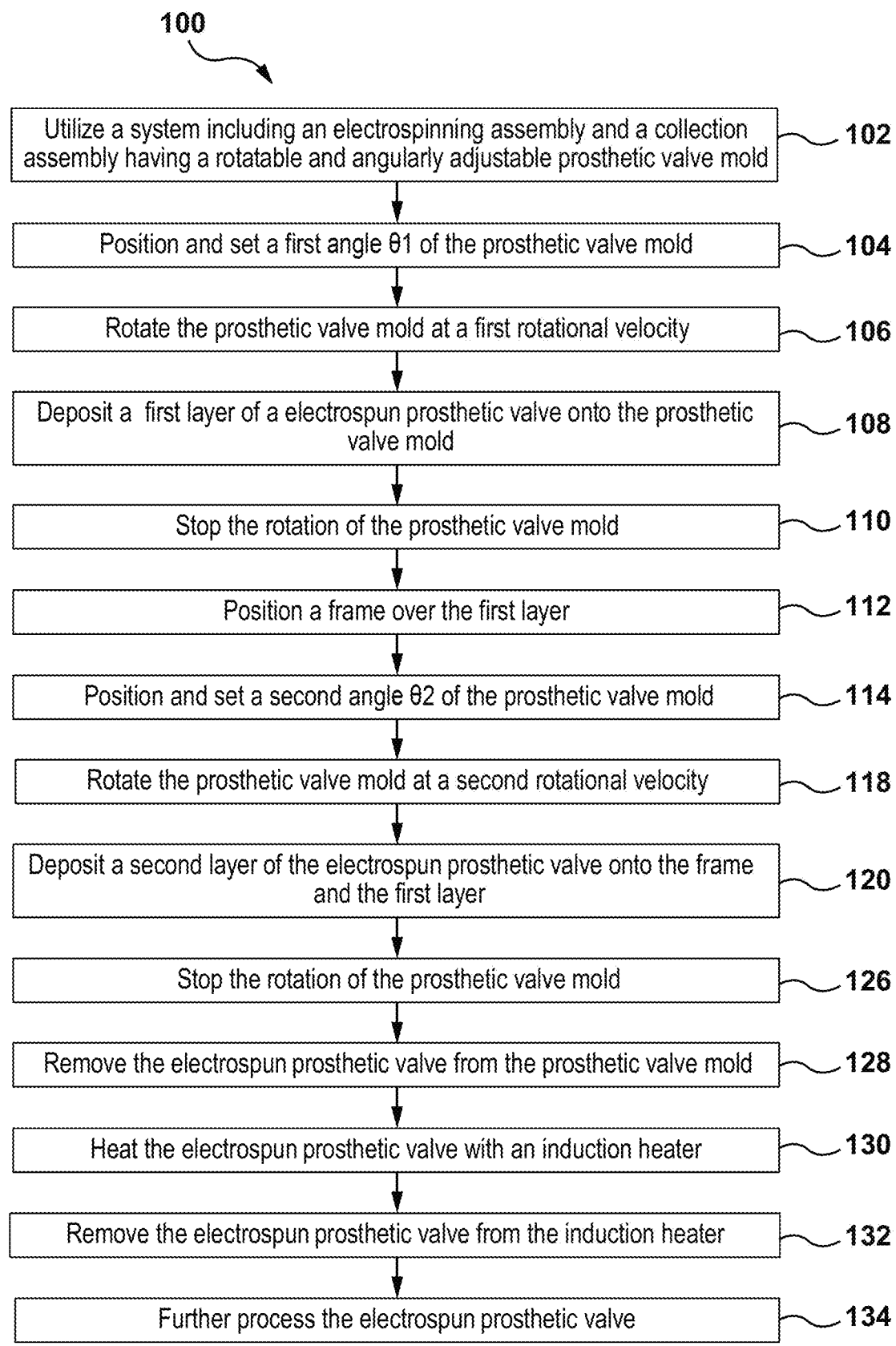
FIG. 1 depicts a flow chart showing steps in a method of making an electrospun prosthetic valve according to an embodiment hereof.

FIG. 1 is a flow chart showing a method 100 of making a medical device such as an electrospun prosthetic valve according to an embodiment hereof. The method as described with respect to FIG. 1 is a method for making a medical device utilizing an "electrospinning process". The term "electrospinning process" refers to a process in which a charged polymer jet forms electrospun fibers that are collected on a grounded mold, as described below. The collected electrospun fibers have diameters in the submicron to micron range. As used herein, the term "diameter" and "diameters" does not have to refer to a circular profile, but instead is used generally to refer to a cross-sectional dimension of the electrospun fibers. The electrospun fibers are extremely biocompatible, and form a porous micro-fiber structure that promotes tissue ingrowth in situ. Further, in an embodiment the electrospun fibers may be biodegradable, producing a tissue engineered electrospun prosthetic valve, wherein the electrospun fibers degrade over time and are replaced by the new tissue ingrowth. Stated another way, the electrospun prosthetic valve is implanted, but over time the implanted electrospun prosthetic valve turns into a tissue valve. In embodiments hereof, the electrospun fibers are formed of a polymer as described below.

Figure 2:
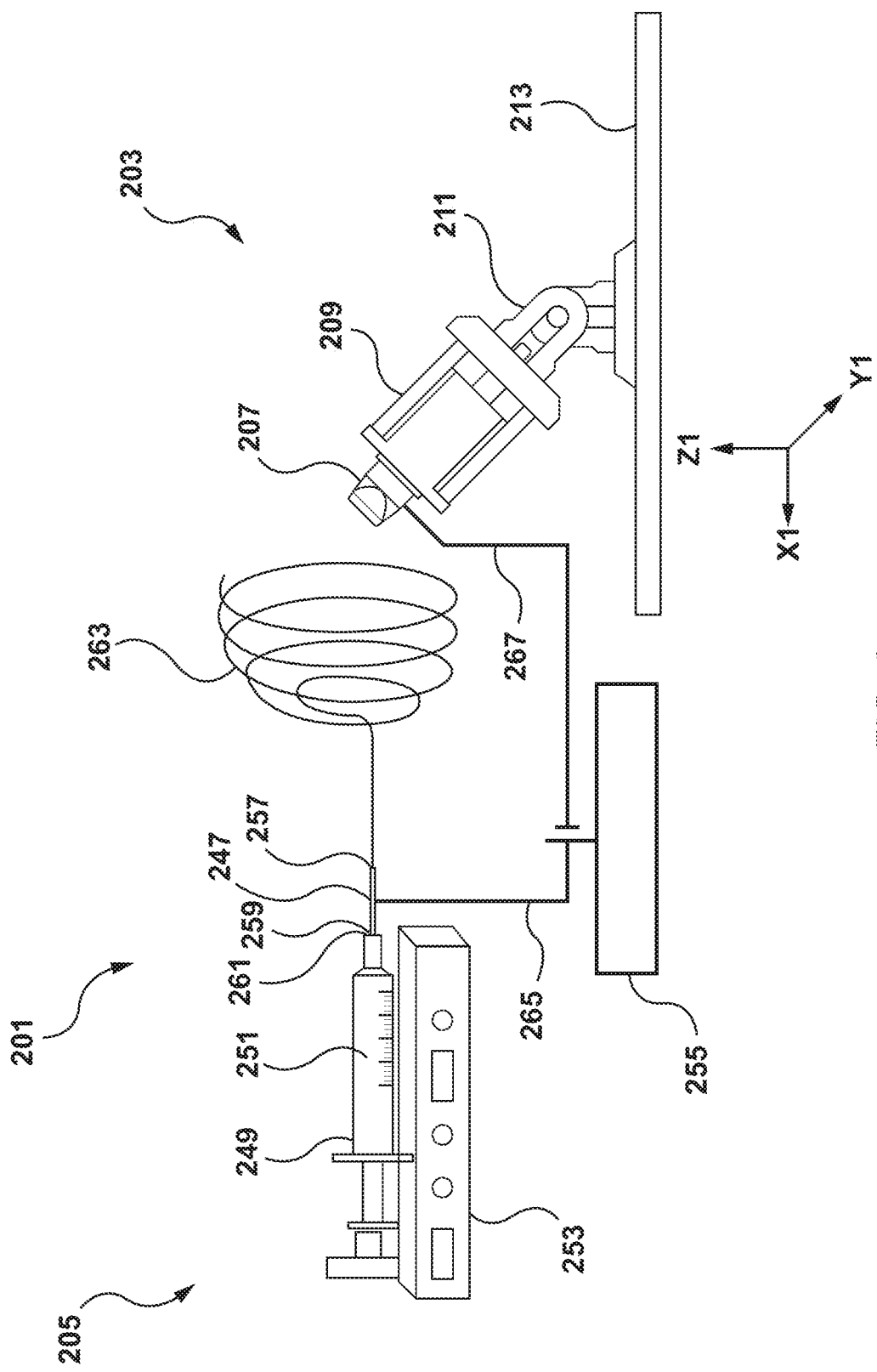
FIG. 2 depicts an illustration of a system for use with the method of FIG. 1 according to an embodiment hereof.

FIG. 2 shows an embodiment of a system 201 for use with the method of FIG. 1. The system 201 includes a collection assembly 203 and an electrospinning assembly 205. The system 201 is configured to form an electrospun prosthetic valve according to embodiments hereof.

Figure 3:
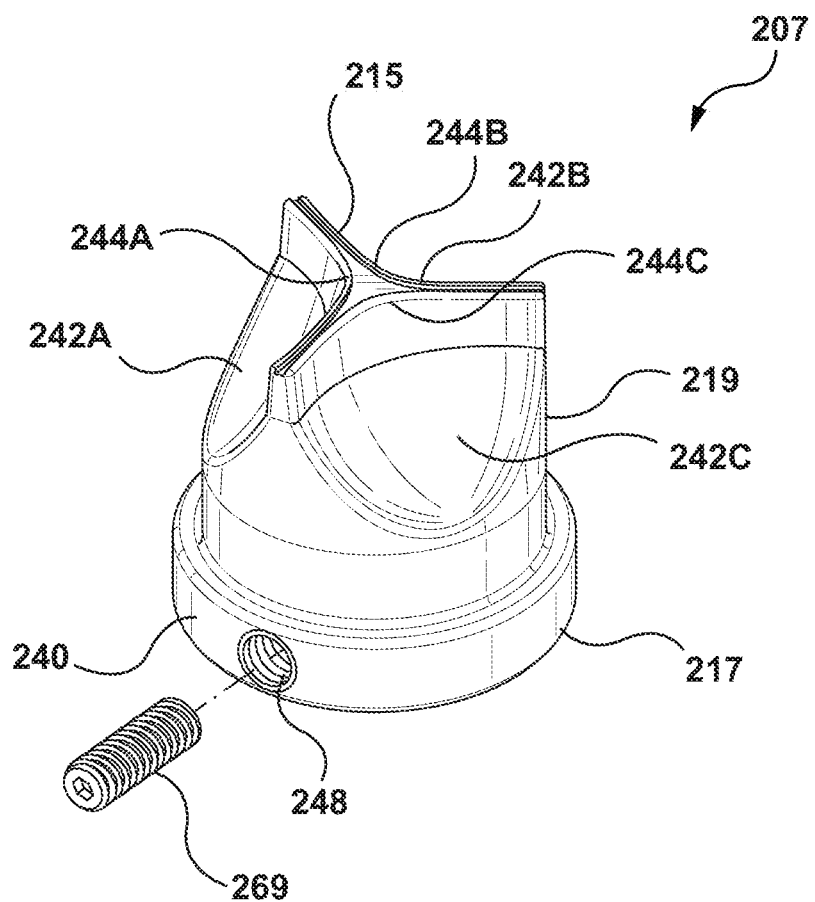
FIG. 3 depicts a perspective illustration of a prosthetic valve mold of the system of FIG. 2 according to an embodiment hereof.

In the embodiment illustrated in FIG. 2, the collection assembly 203 includes a prosthetic valve mold 207, a motor 209, a bracket 211, and a base 213. FIG. 3 shows an embodiment of the prosthetic valve mold 207. The prosthetic valve mold 207 includes a first end 215, a second end 217 opposite the first end 215, a mold base 240, and three segments 242A, 242B, and 242C (together referred to as segments 242). The prosthetic valve mold 207 includes an outer surface 219. The outer surface 219 has a shape or geometry of the desired electrospun prosthetic valve. The shape of the prosthetic valve mold 207 can be selected to improve hydrodynamic properties of the completed electrospun prosthetic valve. Each segment 242 is shaped to form a corresponding leaflet of an electrospun prosthetic valve thereon. Accordingly, while the prosthetic valve mold 207 is illustrated in FIG. 3 with three segments 242A, 242B, 242C, this is by way of example and not limitation. In alternative embodiments, the prosthetic valve mold 207 may include more or fewer segments 242 to correspond to the number of leaflets desired for a particular application of the electrospun prosthetic valve. Further, while the prosthetic valve mold 207 is illustrated as a single unit, this too is by way of example and not limitation. The prosthetic valve mold 207 may be formed of individual components such that the mold base 240, and each of the segments 242A, 242B, and 242C are separate and coupled together to form the prosthetic valve mold 207. Methods of coupling the segments 242A, 242B, and 242C to the mold base 240 can include, but are not limited to adhesives, fusing, welding, mechanical connections, and friction-fit coupling. Further, segments 242A, 242B, 242C, and mold base 240 may be separable from each other such that the electrospun prosthetic valve deposited thereon may be more easily removed from the prosthetic valve mold.

In the embodiment of FIG. 3, the mold base 240 includes a central opening (not shown, but similar to the central opening 447 shown in FIG. 3B) for mounting on a shaft of the motor 209. A threaded aperture 248 is disposed laterally or radially from an outer circumferential surface of the mold base to the central opening. A set screw 269 is disposed through the threaded aperture 248 to the central opening to couple the mold base 240, and hence the prosthetic valve mold 207, to the motor 209. While the set screw 269 is illustrated in FIG. 3 with a specific shape, this is by way of example and not limitation, and the set screw 269 can have other shapes suitable for the purposes described herein. Moreover, the use of the set screw 269 to couple the prosthetic valve mold 207 to the motor 209 is not meant to be limiting, and the prosthetic valve mold 207 can be coupled to the motor 209 by any suitable method such as, but not limited to adhesives, fusing, welding, mechanical coupling, or other suitable methods.

In the embodiment of FIG. 3, the prosthetic valve mold 207 further includes three (3) channels 244A, 244B, 244C (collectively referred to herein as "channels 244"). The channels 244 form corresponding channels in the precursor electrospun prosthetic valve formed thereon. The channels 244 are configured to facilitate easy separation of the leaflets of the electrospun prosthetic valve to create free edges for opening and closing of the leaflets, as described below. In the embodiment shown in FIG. 3, the channels 244 form a single contiguous channel. However, this is not required. Further, in other embodiments, the channels 244 can be omitted.

As noted above, the segments 242A, 242B, 242C of the prosthetic valve mold 207 may be separable from each other and the mold base 240. In a particular embodiment of a prosthetic valve mold 407 including a mold base 440 and segments 442, shown in FIGS. 3A and 3B, each segment 442 includes a leaflet portion 443 and a stem 445. Thus, the segments 442A, 442B, 442C include leaflet portions 443A, 443B, 443C and stems 445A, 445B, 445C, respectively. The mold base 440 includes stem openings 441A, 441B, 441C that are sized and shaped to receive a respective one of the stems 445A, 445B, 445C to seat the corresponding segment 442A, 442B, 442C therein. The base 440 also includes threaded openings 449A, 449B, 449C, with each opening extending laterally or radially from a circumferential outer surface of the mold base 440 to a corresponding one of the stem openings 441A, 441B, 441C. The corresponding stem 445A, 445B, 445C of each segment 442A, 442B, 442C is placed in the corresponding stem opening 441A, 441B, 441C of the base 440, and a set screw 471A, 471B, 471C is inserted into the corresponding threaded opening 449A, 449B, 449C to secure the segments 442A, 442B, 442C to the mold base 440. While the set screws 471A, 471B, 471C are illustrated in FIGS. 3A and 3B with a specific shape, this is by way of example and not limitation. The set screws 471A, 471B, 471C can each have other shapes suitable for the purposes described herein. Other ways to removably secure the segments 442A, 442B, 442C to the mold base 440 may be utilized. The mold base 440 also includes a central opening 447 which is sized and shaped to fit onto a shaft of the motor 209. The mold base 440 further includes a threaded opening 448 extending laterally or radially from an outer cylindrical surface of the base 440 to the central opening 447. A set screw 469 extends through the threaded opening 448 to the central opening 447 to secure the valve mold 407 to the motor 209. The set screw 469 is similar to the set screw 269 previously described with respect to FIG. 3 and is not meant to be limiting and other ways to secure the valve mold 407 to the motor 209 may be utilized.

The valve mold 407 has been described with particular reference to separable segments 442. However, the features or other embodiments of valve molds described herein, such a valve molds 207, 507 may be utilized with the valve mold 407. For example, and not by way of limitation, the valve mold 407 may include channels such as channels 244 described with respect to valve mold 207. Further, portions of the valve mold 407 may be heated as described with respect to valve mold 507 below.

Figure 3C:
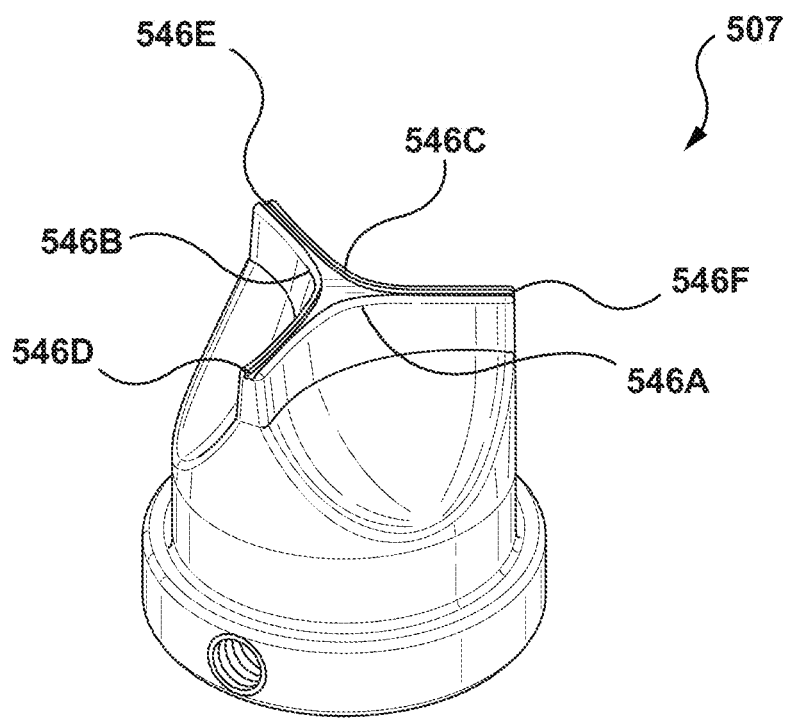
FIG. 3C depicts a perspective illustration of a prosthetic valve mold of the system of FIG. 2 according to another embodiment hereof, wherein the prosthetic valve mold includes a plurality of heatable first sections.

FIG. 3C illustrates a prosthetic valve mold 507 according to another embodiment hereof. The prosthetic valve mold 507 is similar to the prosthetic valve mold 207 described above. Therefore, details of the prosthetic valve mold 507 not specifically described with respect to this embodiment are as described with respect to prosthetic valve mold 207 and/or prosthetic valve mold 407. In the prosthetic valve mold 507, a plurality of heated portions 546A, 546B, 546C, 546D, 546E, and 546F (collectively referred to herein as "heated portions 546") of the prosthetic valve mold 507 are heated. The heated portions 546 of the prosthetic valve mold 507 are configured to melt corresponding selected portions of an electrospun prosthetic valve disposed thereon. The temperature of the heated portions 546 of the prosthetic valve mold 507 are precisely controlled. For example, and not by way of limitation, the heated portions 546 of the prosthetic valve mold 507 can be heated to a temperature in a range of 60° to 160° Celsius. Areas of the valve mold 507 may be heated where it is desirable to crystallize the electrospun fibers deposited thereon to improve strength, but not crystallize areas of the valve mold 507 where it is desirable for the electrospun fibers deposited thereon to maintain the porous, microfiber thereof to promote tissue ingrowth when the electrospun prosthetic valve is deployed. Thus, in one particular embodiment shown in FIG. 3C, the heated portions 546 of the prosthetic valve mold 507 correspond to free edges and commissures of the electrospun prosthetic valve formed on the prosthetic valve mold 507. The heated portions 546A, 546B, 546C of the valve mold 507 are areas where the free edges of the leaflets of the electrospun prosthetic valve are formed, and heated portions 546D, 546E, 546F are areas of the valve mold 507 where commissures of the electrospun prosthetic valve are formed. The free edges and commissures of a prosthetic valve endure high stress during use such that increased strength in these areas would be desirable, whereas the body of the leaflets would not crystallize to maintain the porous, microfiber structure of the electrospun fibers. However, this is not meant to be limiting, and other areas of the prosthetic valve mold 507 can be heated, in any combination.

In a non-limiting example, the heated portions 546 of the prosthetic valve mold 507 are precisely and controllably heated via conduction of heat from the motor 209 (visible in FIG. 2) as the prosthetic valve mold 507 is rotated at high speed. In a non-limiting example for controlling the heat from the motor 209, the prosthetic valve mold 507 can be formed using a combination of insulating and conducting materials. Thus, when in use, the conductive areas of the prosthetic valve mold 507 heat up due to heat from the motor 209, while the insulated areas of the prosthetic valve mold 507 remain cool. In another non-limiting example, targeted heating elements could be coupled to the heated portions 546 of the prosthetic valve mold 507 to heat the heated portions 546, while areas without heating elements would not be heated. Alternatively, the heated portions 546 of the prosthetic valve mold 507 can be heated by other methods including, but not limited convection, radiation, or any other method suitable for the purposes described herein.

The prosthetic valve mold 507 of FIG. 3C has been described with respect to the heated portions 546. Thus, the undescribed portions of prosthetic valve mold 507 may include features and alternatives from the embodiments of the prosthetic valve mold 207 or the prosthetic valve mold 407. For example, and not by way of limitation, the prosthetic valve mold 507 may include separable portions as described with respect to prosthetic valve mold 407. Further, any of the prosthetic valve molds described herein may include heated portions as described with respect to prosthetic valve mold 507.

Figure 4:
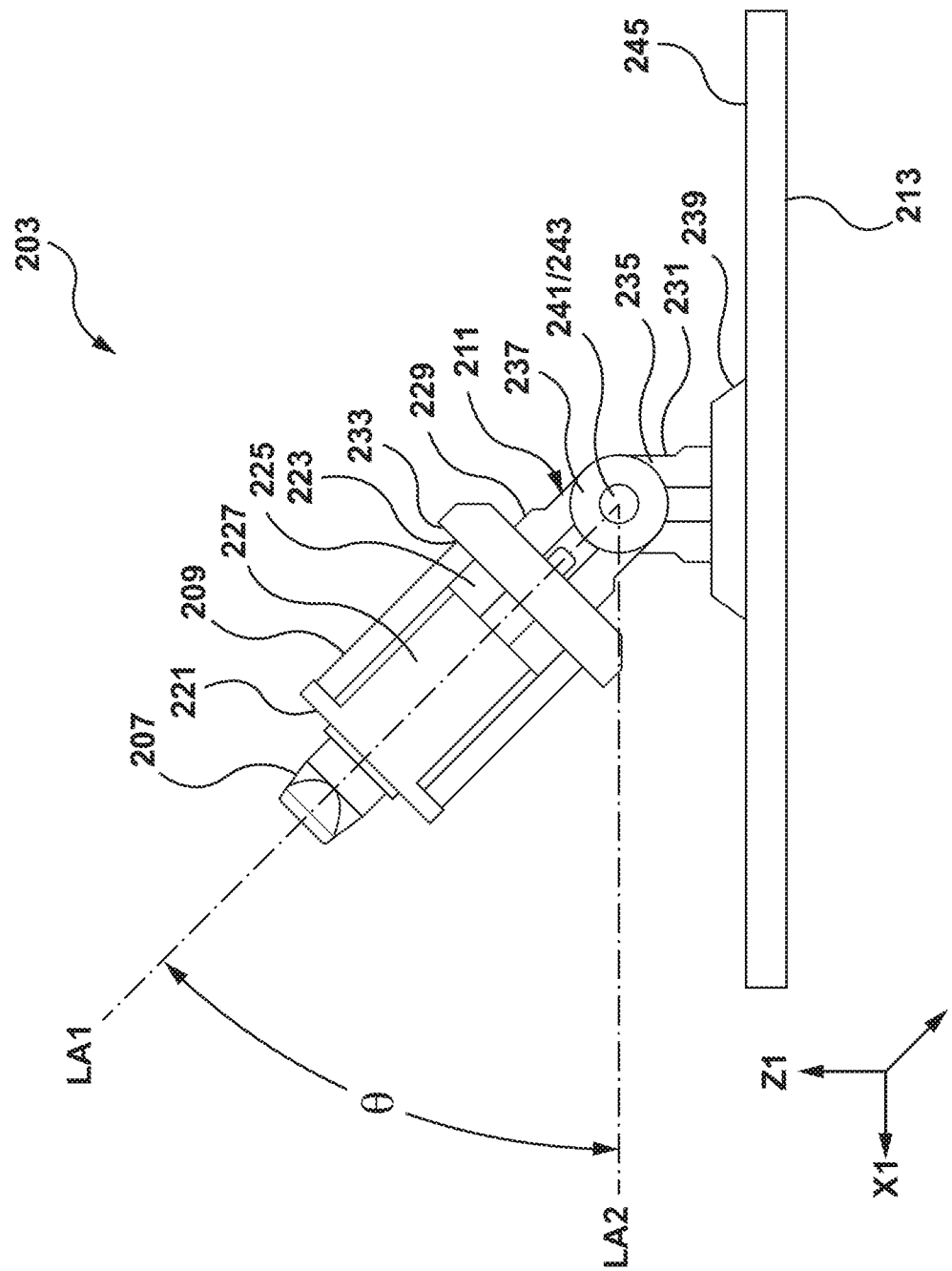
FIG. 4 depicts an illustration of a collection assembly of the system of FIG. 2 according to an embodiment hereof.

The prosthetic valve molds 207, 407, 507 are configured to be rotatable and angularly adjustable. For convenience, when describing the interaction of the prosthetic valve mold with other parts of the system 201, the prosthetic valve mold 207 will be referenced. However, such reference is not meant to be limiting such that any of the valve molds 207, 407, 507 may be utilized with the system 201. In the embodiment of FIGS. 2-4, the prosthetic valve mold 207 is rotatable via the motor 209 and angularly adjustable via the bracket 211 as described below. The prosthetic valve mold 207 is further configured to act as a conductive substrate onto which a plurality of electrospun fibers 263 from the electrospinning assembly 205 are collected as described below. In an embodiment, the prosthetic valve mold 207 is metallic and is formed of materials such as, but not limited to stainless steel, aluminum, cobalt chromium, and titanium. The prosthetic valve mold 207 can be formed by methods such as, but not limited to, 3D printing, casting, machining, or any other suitable method.

FIG. 4 shows the motor 209 of the system 203, which includes a first end 221, a second end 223 opposite the first end 221, and an outer surface 225. The first end 221 of the motor 209 is coupled to the second end 217 of the prosthetic valve mold 207. The motor 209 is configured to rotate the prosthetic valve mold 207 to permit desired deposition or distribution of the electrospun fibers 263 from the electrospinning assembly 205 onto the outer surface 219 of the prosthetic valve mold 207. The motor 209 may be of any design suitable for the purposes described herein and capable of rotating the coupled prosthetic valve mold 207 at desired rotational velocities, for example, and not by way of limitation, in a range of 0-1,000 revolutions per minute (RPM). In an embodiment, the motor 209 can be a stepper motor precisely controlled using a programmable stepper motor amplifier. Alternatively, in another embodiment the motor 209 can be a servo motor controlled using a sensor and a servo controller.

The motor 209 may include an insulating material 227 on the outer surface 225, as shown in FIG. 4. The insulating material 227 is configured to minimize effects of the electric field generated by the motor 209 that could interfere with the deposition of the electrospun fibers 263 onto the prosthetic valve mold 207 in the method of FIG. 1. Non-limiting examples of the insulating material 227 include rubber, paper, polyvinylchloride, varnish, silicone, and resin. The insulating material 227 can be coupled to the outer surface 225 of the motor 209 by methods such as, but not limited to adhesives, mechanical couplings, or any other suitable coupling methods.

The bracket 211 includes a first portion 229, and second portion 231, as illustrated in FIG. 4. The first portion 229 includes a first end 233 coupled to the second end 223 of the motor 209, and a second end 235 pivotably coupled to a first end 237 of the second portion 231 at a pivot joint 241. The second portion 231 further includes a second end 239, which is coupled to the base 213. The bracket 211 is configured to enable the first portion to be angularly adjustable relative to the second portion 231, thereby enabling adjustment of the motor 209 and the rotating prosthetic valve mold 207 to an angle □ to evenly distribute electrospun fibers 263 onto the rotating prosthetic valve mold 207 in an electrospinning process as described below. The bracket 211 includes a first or unlocked configuration wherein the angle □ can be adjusted, and a second or locked configuration wherein the angle □ is static, fixed, or locked. Accordingly, when the bracket 211 is in the unlocked configuration, the first portion 229 is pivotable about the pivot joint 241, and moves or pivots relative to the second portion 231. When the bracket 211 is in the locked configuration, the first portion 229 is not pivotable about the pivot joint 241, and does not move or pivot relative to the second portion 231. Accordingly, the pivot joint 241 is lockable via a locking mechanism 243 such that the bracket 211 may transition between the unlocked configuration and the locked configuration. Various types of locking mechanisms 243 can be utilized at the pivot point 241, non-limiting example of which include a helical or threaded screw, a cam-lock, or any other suitable locking mechanism. In a non-limiting example, when the bracket 211 is in the first configuration, the first portion 229 is pivotable about the pivot point 241 such that the angle □ of the first portion 229, and more precisely the first longitudinal axis LA1 of the prosthetic valve mold 207, can be adjusted within a range of 0°-180° relative to a second longitudinal axis LA2 extending through the pivot point 241 and parallel to the collection base 213, as illustrated in FIG. 4.

While the bracket 211 is illustrated with a specific shape in FIGS. 2 and 4, this is by way of example and not limitation. The shape of the bracket 211 and the first and second portions 229, 231 can be of any suitable design permitting adjustment of the angle □ as previously described. Further, the bracket 211 may be formed of any suitable material such as, but not limited to aluminum, stainless steel, or plastics.

As illustrated in the embodiment of FIG. 4, the collection assembly 203 further includes the base 213. The base 213 is configured to provide a stable platform onto which the second end 239 of the second portion 231 of the bracket 211 is coupled, and accordingly to which the motor 209 and the prosthetic valve mold 207 are effectively mounted. In an embodiment, the bracket 211 may be mounted to the base 213 in various orientations and locations relative to three planes X1, Y1, and Z1, to enable desired positioning of the prosthetic valve mold 207 relative to the electrospinning assembly 205. Proper positioning and manipulation of the prosthetic valve mold 207 enables even distribution or deposition of the plurality of electrospun fibers 263 onto the prosthetic valve mold 207. The second portion 231 of the bracket 211 may be coupled to a first surface 245 of the base 213 by methods such as, but not limited to adhesives, screws, mechanical couplings, or any other methods suitable for the purposes described herein. The base 213 may be formed of any suitable material, non-limiting examples of which include plastics, aluminum, and wood. In an embodiment, the base 213 may be a breadboard with multiple openings for mounting the bracket 211 in various locations, as will be understood by persons knowledgeable in the art. In another embodiment, the base 213 can be a movable XYZ stage. While the base 213 is illustrated in FIG. 2 with a rectangular and planar shape, this is by way of example and not limitation. The base 213 may have other shapes including, but not limited to a circular shape, an oval shape, or any other suitable shape.

Referring back to FIG. 2, the electrospinning assembly 205 will now be described. The electrospinning assembly 205 is a simplified exemplary embodiment suitable for the purposes described herein. The electrospinning assembly 205 includes a needle 247, a syringe 249, a polymer solution 251, a syringe pump 253, and a power supply 255. The needle 247 includes a first end 257 and a second end 259. The second end 259 of the needle 247 is coupled to a first end 261 of the syringe 249. The polymer solution 251 is disposed within the syringe 249 and the needle 247. In an embodiment, the polymer solution 251 includes a polymer and a solvent. The polymer can be any suitable polymer such as, but not limited to polycaprolactone (PCL), polylactic acid (PLLA), polytrimethylene carbonate (PTMC), polyurethane (PU), block copolymers such as polyactic acid-polycaprolactone-polyactic acid (PLLA-PCL-PLLA), and polymer blends such as polycaprolactone/polyactic acid (PCL/PLLA). The solvent can be any suitable solvent, non-limiting examples of which include chloroform, dimethylformamide (DMF) and acetic acid. In a non-limiting example, the polymer solution 251 is 15% polymer by weight. The syringe pump 255 is configured to controllably release the polymer solution 251 from the first end 257 of the needle 247. While the electrospinning process is described as utilizing the polymer solution 251, which is a combination of a polymer and a solvent, this is by way of example and not limitation. In an alternative embodiment, an electrospinning process can include melt-spinning wherein the polymer is heated to a liquid state before ejection from the needle 247. The power supply 255 is electrically coupled to the needle 247 via the first connection 265 and further electrically coupled to the prosthetic valve mold 205 of the collection assembly 203 via the second connection 267. In an embodiment, the power supply 255 is configured to supply a first electrical force to the needle 247 to charge the polymer solution 251 dispensed from the needle 247. The power supply 255 is further configured to place a second electrical force on the prosthetic valve mold 205. The first and the second electrical forces can each be selected to control the attraction of the polymer solution 251 to the valve mold 205 to thereby optimize the even distribution of electrospun fibers 263 thereon, as described below. For example, and not by way of limitation, the first electrical force on the needle 247 can be −10 kV and the second electrical force on the prosthetic valve mold 205 can be 0 kv, or grounded. The first and second connections 265, 267 may be any electrical conductor suitable for the purposes described herein. For example, and not by way of limitation, each of the first and second connections 265, 267 can be a copper wire. While the second connection 267 is shown disposed external of the collection assembly 203, it is understood that the second connection 267 may be disposed within portions of the collection assembly 203.

The operation of the system 201 to generate the plurality of electrospun fibers 263 will now be described with reference to FIG. 2. The syringe pump 253 controls the release of the polymer solution 251 from the first end 259 of the needle 247. The power supply 255 induces a charge on the polymer solution 251 at the first end 257 of the needle 247. When the induced charge overcomes the surface tension of the polymer solution 251 at the first end 257 of the needle 247, a jet or stream of the polymer solution 251 is ejected. Acceleration of the jet of the polymer solution 251 through the electric field generated by the power supply 255 causes elongation and thinning of the jet of the polymer solution 251. The electric field generated by the power supply 255 further causes solvent of the polymer solution 251 to evaporate and to thereby produce the plurality of electrospun fibers 263.

FIGS. 5-13 illustrate steps of a method of manufacturing an electrospun prosthetic valve according to an embodiment hereof. As noted above, references to the valve mold 207 is for convenience only and is not meant to be limiting. Any of the valve molds described herein may be used in the method described. In a first step 102, a system, such as the system 201 of FIG. 2, including the electrospinning assembly 205 and the collection assembly 203 is utilized. The collection assembly 203 includes the rotatable and angularly adjustable prosthetic valve mold 207. In FIGS. 5, 6, 8, and 10, only the needle 247 of the electrospinning assembly 205 is illustrated, with the remainder of the electrospinning assembly 205 omitted for clarity.

Figure 5:
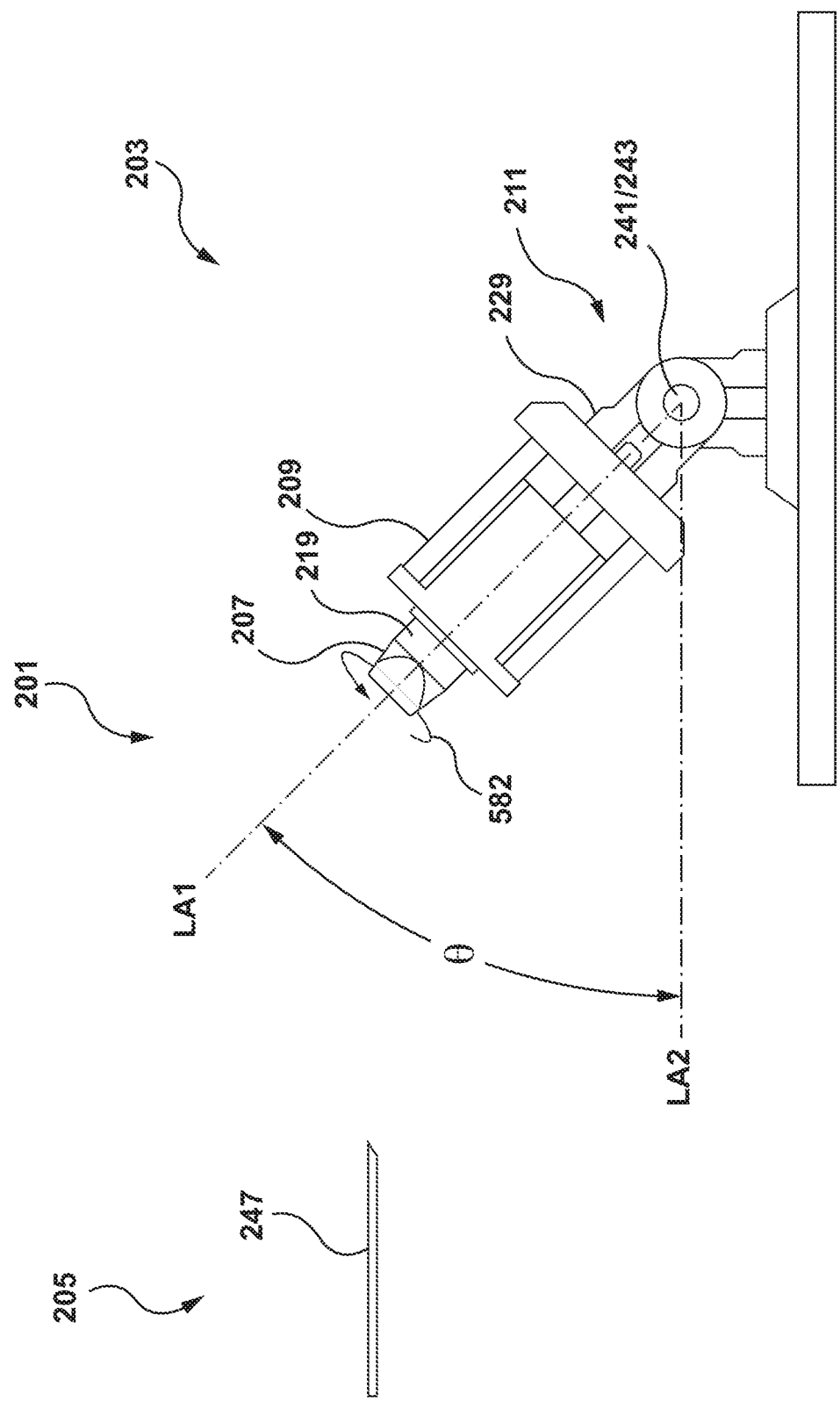
FIG. 5 depicts a step in the method of FIG. 1, wherein a first angle of the prosthetic valve mold is adjusted.

Referring to FIG. 5, in a next step 104 the prosthetic valve mold 207 is positioned at a desired location and angle relative to the electrospinning assembly 205. More specifically, the prosthetic valve mold 207 is adjusted to a first angle □1 and position on the base 213 at a desired location to enable an even distribution of a first plurality of electrospun fibers 263A onto the prosthetic valve mold 207 of the collection assembly 203, as described below. Adjustment of the first angle □1 of the prosthetic valve mold 207 is accomplished by manipulating the locking mechanism 243 to transition the bracket 211 from the second or locked configuration to the first or unlocked configuration. When the bracket 211 is in the unlocked configuration, the prosthetic valve mold 207, the motor 209, and the first portion 229 of the bracket 211 is pivoted about the pivot joint 241 to position the prosthetic valve mold 207 at the first angle □1. When the prosthetic valve mold 207 is at the first angle □1, the locking mechanism 243 is manipulated to transition the bracket 211 from the unlocked configuration to the locked configuration.

In a next step 106, with the prosthetic valve mold 207 is at the desired position and the first angle □1, the motor 209 is engaged to rotate the prosthetic valve mold 207 in a first direction, as illustrated by the an arrow 582 in FIG. 5. The prosthetic valve mold 207 is rotated at a first rotational velocity RV1. The first rotational velocity RV1 is selected to permit the even distribution of the first plurality of electrospun fibers 263A onto the outer surface 219 of the prosthetic valve mold 207.

Figure 6:
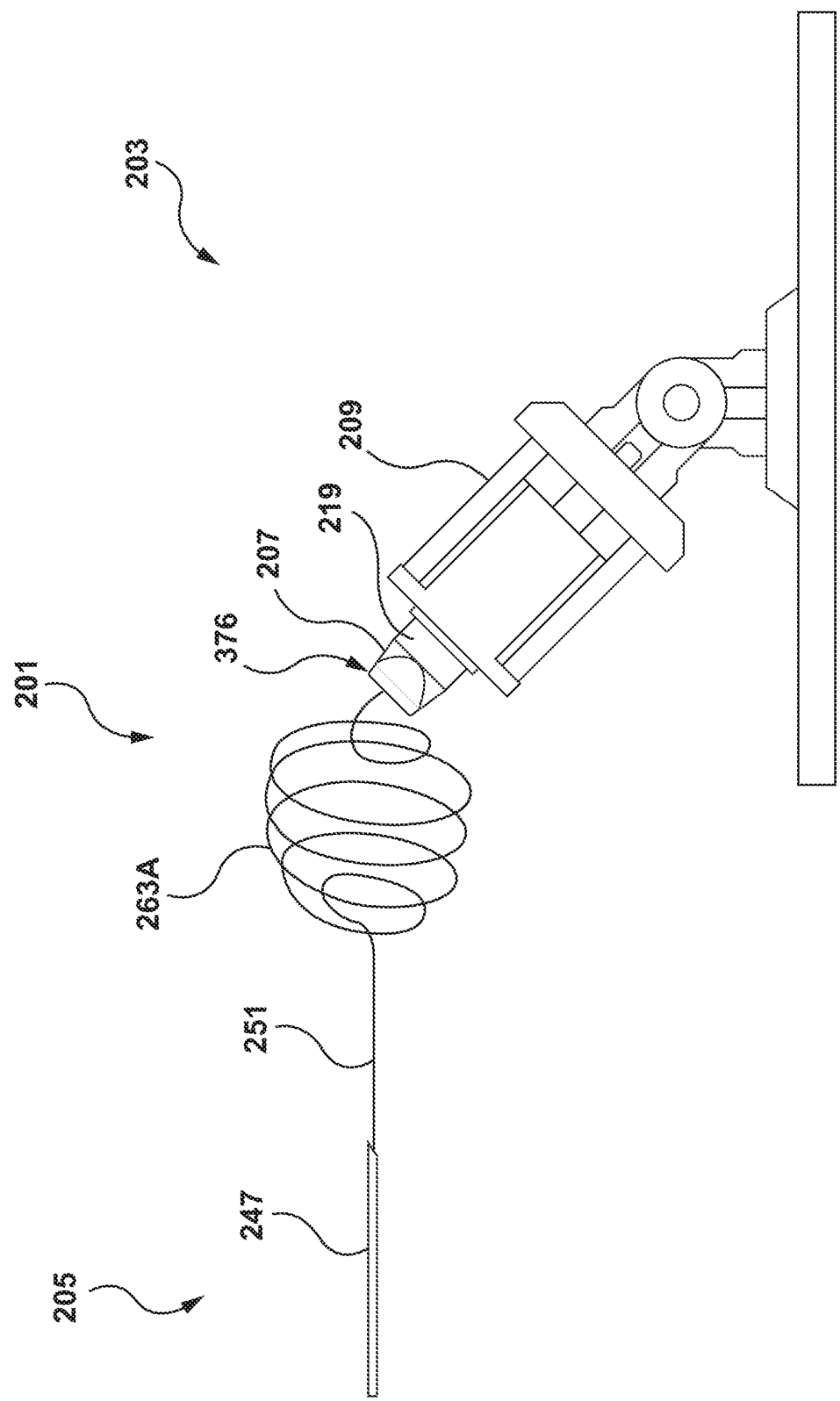
FIG. 6 depicts a step in the method of FIG. 1, wherein a first layer of an electrospun prosthetic valve is deposited on the prosthetic valve mold.
Figure 7:
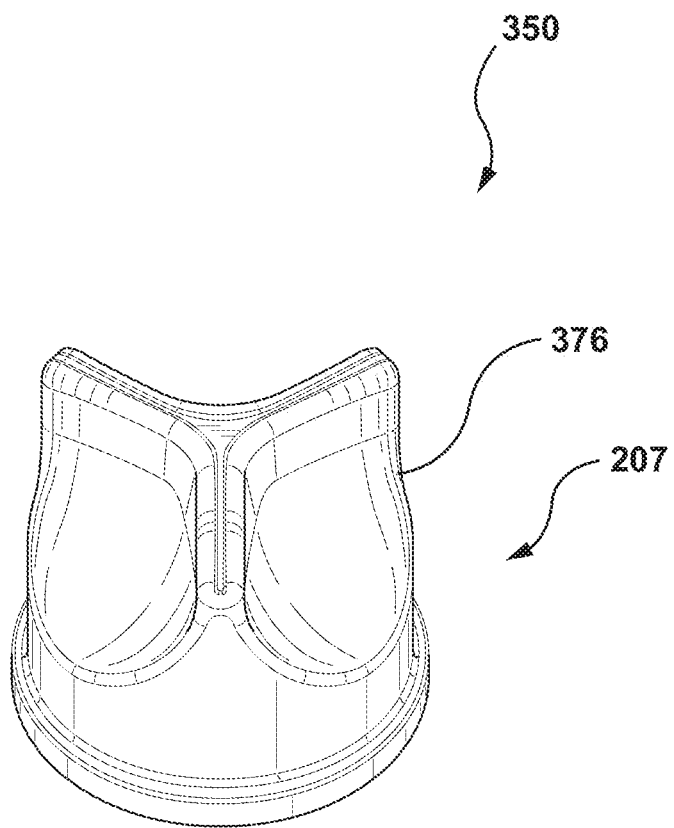
FIG. 7 depicts a perspective illustration of the first layer of the electrospun prosthetic valve.

As illustrated in FIG. 6, when the prosthetic valve mold 207 is positioned and rotating as desired, the electrospinning assembly 205 is engaged to deposit the first plurality of electrospun fibers 263A onto the prosthetic valve mold 207 in a next step 108. The first plurality of electrospun fibers 263A form a first layer 376 of an electrospun prosthetic valve 350. More specifically, the electrospinning assembly 205 creates a charge jet of polymer solution 251 from the needle 247. As previously described with respect to the system 201 of FIG. 2, the charged jet of polymer solution 251 elongates to form the first plurality of electrospun fibers 263A, which are deposited, distributed, or collected on the outer surface 219 of the rotating prosthetic valve mold 207. Stated another way, the first plurality of electrospun fibers 263A are collected on the prosthetic valve mold 207 in an even distribution to form the first layer 376, as best illustrated in FIG. 7. The first layer 376 of the electrospun prosthetic valve 350 may also be referred to as a valve layer or a leaflet layer.

With the first layer 376 deposited on the prosthetic valve mold 207, in a next step 110 the motor 209 of the collection assembly 203 is disengaged such rotation of the prosthetic valve mold 207 and the first layer 376 collected thereon is stopped.

Figure 8:
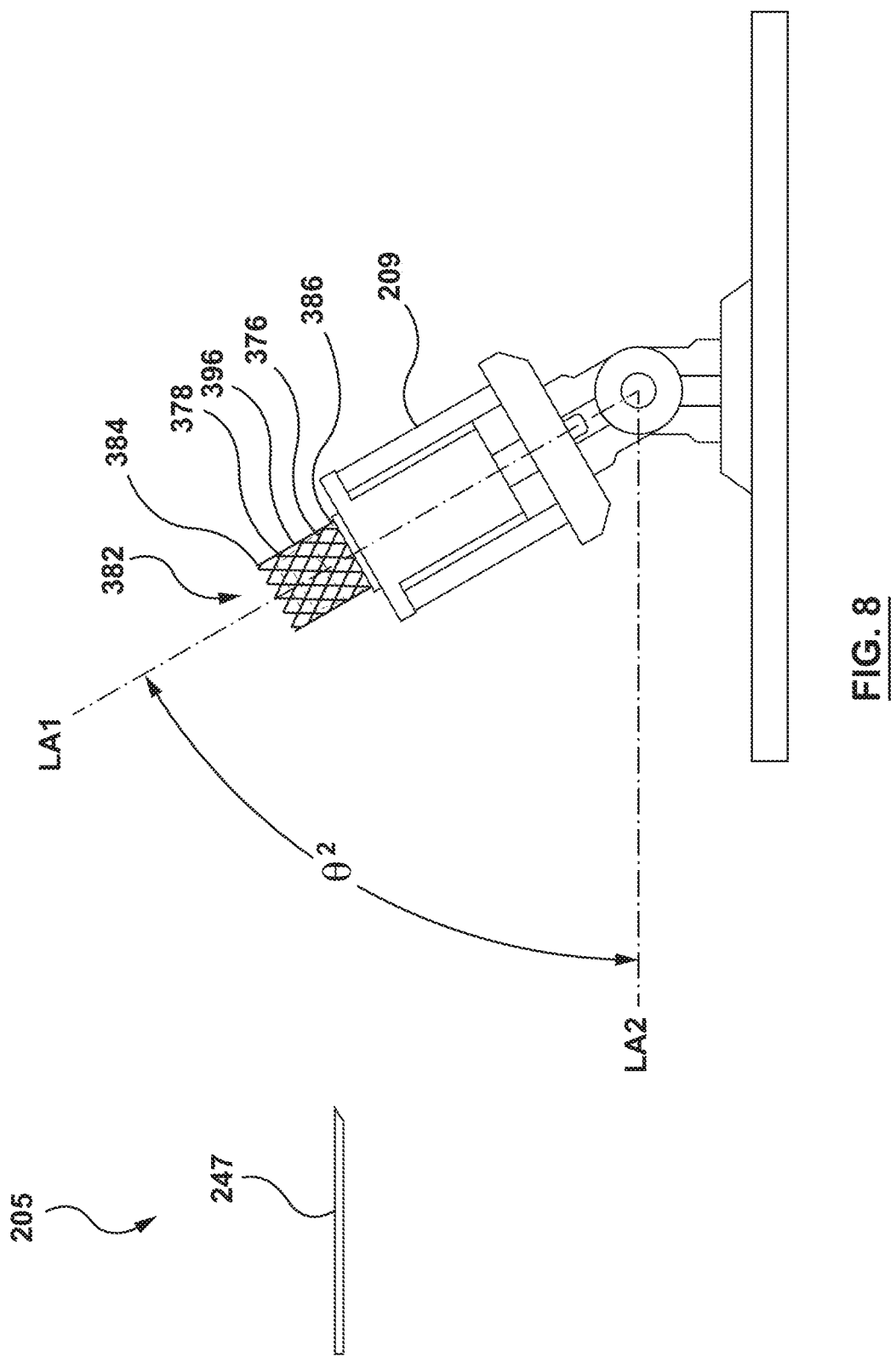
FIG. 8 depicts a step in the method of FIG. 1, wherein a frame is positioned on an outer surface of the first layer.
Figure 9:
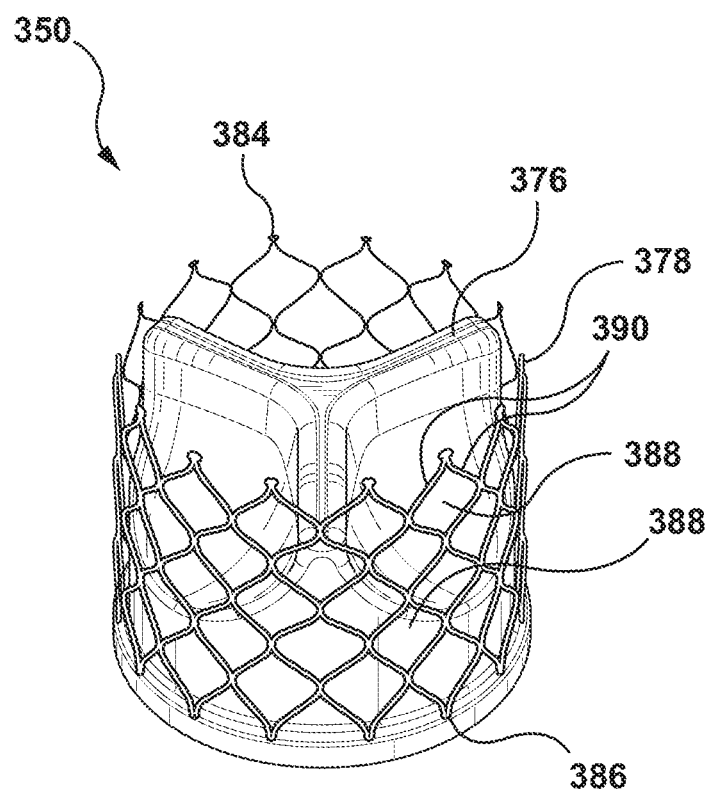
FIG. 9 depicts a perspective illustration of the frame positioned over the first layer of the electrospun prosthetic valve.

In a next step 112 illustrated in FIG. 8, a frame 378 is positioned on an outer circumferential surface 396 of the first layer 376. Stated another way, the frame 378 is slipped or slid over the first layer 376 such that the first layer 376 is disposed within a lumen 382 of the frame 378. The frame 378 is a generally tubular structure and includes the lumen 382 extending from a first or inflow end 386 to a second or outflow end 384. The lumen 382 of the frame 378 is configured and sized to receive the first layer 376 of the electrospun prosthetic valve 350. In an embodiment, the frame 378 further includes a plurality of cells 388 formed by a plurality of struts 390, as shown for example in FIG. 9. In an embodiment, the frame 378 is self-expanding to return to a radially expanded configuration from a radially compressed configuration. The frame 378 may be formed from a variety of materials including, but not limited to stainless steel, nickel-titanium alloys (e.g. NITINOL), or other suitable materials. "Self-expanding", as used herein refers to a structure having a mechanical memory to return to the radially expanded configuration. Mechanical memory may be imparted on the structure that forms the 378 using techniques understood in the art. While the frame 378 is shown with the plurality of equally sized cells 388, this is by way of example and not limitation. In an alternative embodiment, the cells 388 of the frame 378 may be of a variety of sizes and may be distributed in any suitable pattern.

Figure 10:
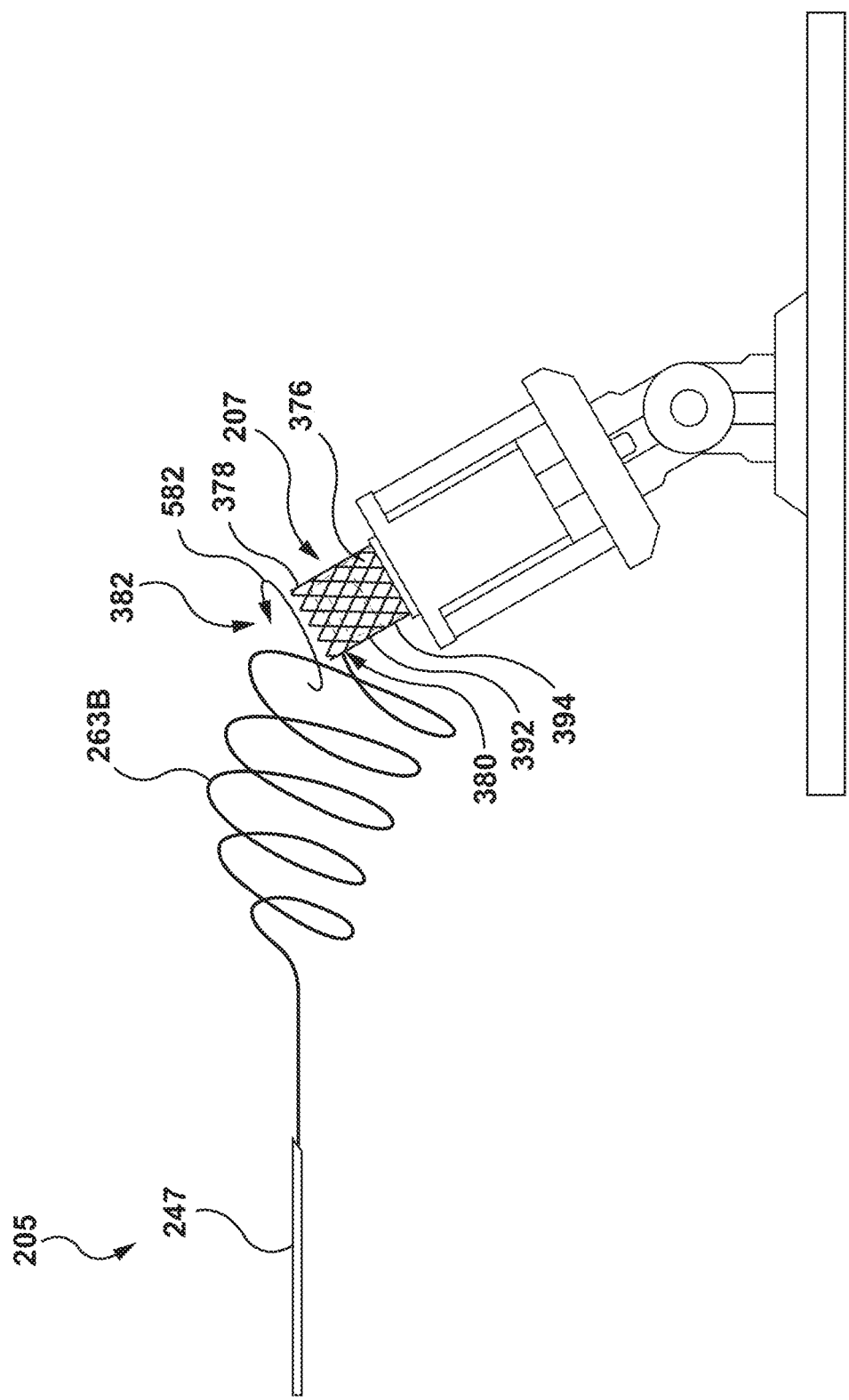
FIG. 10 depicts a step in the method of FIG. 1, wherein a second layer of the electrospun prosthetic valve is deposited on an outer surface of the frame and the outer surface of the first layer.

Referring next to FIG. 10, with the frame 378 properly positioned about the first layer 376, in a next step 114 the prosthetic valve mold 207 is again positioned at a desired location and angle relative to the electrospinning assembly 205. More specifically, the prosthetic valve mold 207 is adjusted to a second angle ☐2 and bracket 211 is positioned at a desired location and orientation on the base 213 to enable an even distribution of a second plurality of electrospun fibers 263B, as described below. Adjustment of the second angle ☐2 of the prosthetic valve mold 207 is accomplished as previously described with respect to step 104. In embodiments hereof, the second angle ☐2 can be the same as the first angle ☐1, or can be a different angle. The angles ☐1 and ☐2 are set to enable even distribution of the first and second layers 376, 380 onto the prosthetic valve mold 207.

When the prosthetic valve mold 207 is adjusted to the second angle ☐2, in a next step 118 the motor 209 is engaged to rotate the prosthetic valve mold 207, including the first layer 376 and the frame 378, in the first direction illustrated by the arrow 582 at a second rotational velocity RV2. As previously described with reference to the step 106 and FIG. 5, the second rotational velocity RV2 is selected to enable the even distribution of the second plurality of electrospun fibers 263B. While the step 118 is described as rotating the prosthetic valve mold 207 in the first direction, this is by way of example and not limitation. It shall be understood that the step 118 could alternatively rotate the prosthetic valve mold 207 in a second direction opposite the first direction. Further, while the method 100 is described herein with the first and the second rotational velocities RV1 and RV2, the first and second rotational velocities can be equivalent velocities, or they can each be a different velocity.

Figure 11A:
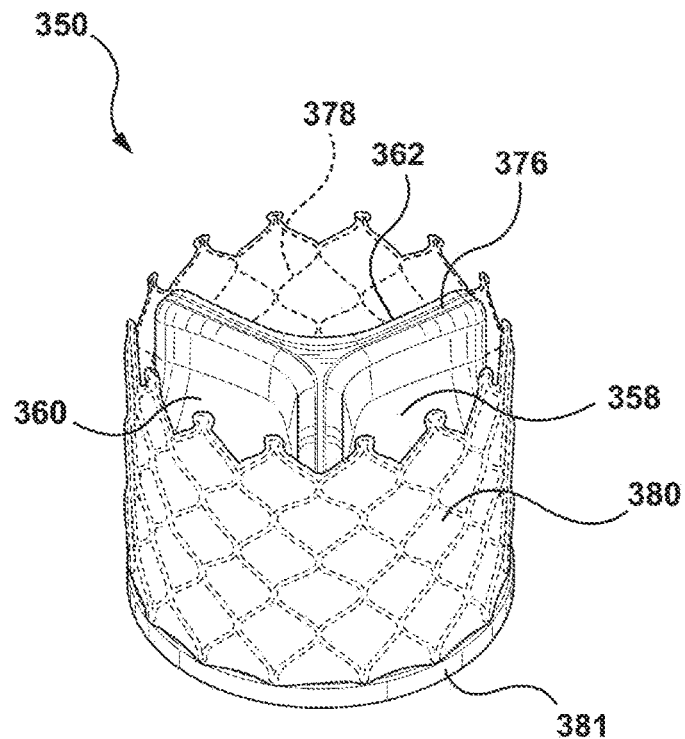
FIG. 11A depicts a perspective illustration of the second layer disposed over the frame and the first layer.
Figure 11B:
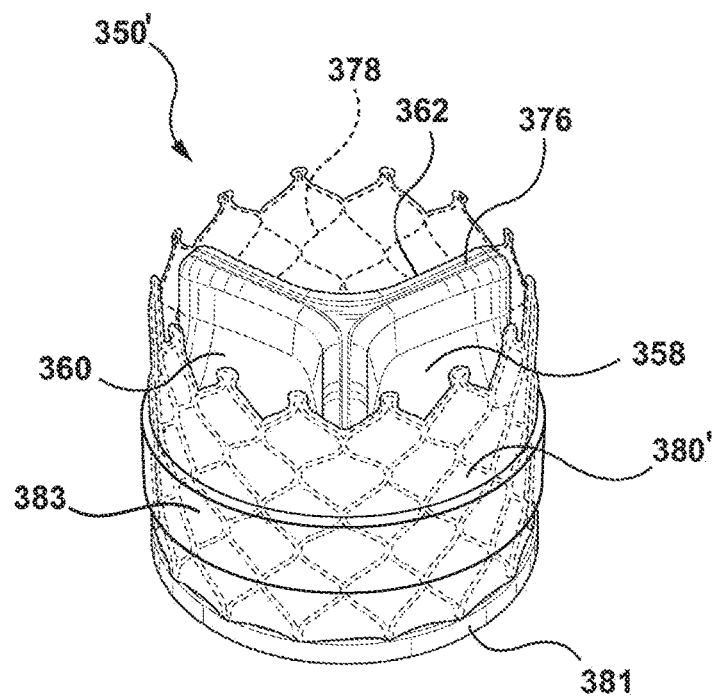
FIG. 11B depicts a perspective illustration of an alternate second layer having an area of increased thickness disposed over the frame and the first layer.

With the prosthetic valve mold 207, including the first layer 376 and the frame 378, positioned and rotating as desired, in a next step 120 the electrospinning assembly 205 is engaged. As previously described with respect to the first layer 376 in step 108, engagement of the electrospinning assembly 205 forms the second plurality of electrospun fibers 263B that are deposited on an outer surface 392 of the first layer 376 and the outer surface 394 of the frame 378 to form the second layer 380 of the electrospun prosthetic valve 350. The second layer 380 may also be referred to as a skirt or anti-PVL (anti-paravalvular leakage) layer. The second layer 380 can have a uniform diameter along a length of the prosthetic valve 350 (FIG. 11A) or can be defined as an area of increased thickness 383 with respect to other regions of the second layer 380' (FIG. 11B). The area of increased thickness or anti-PVL layer 383 can be positioned at any area along the second layer 380', as desired. The prosthetic valve 350' is otherwise identical to and is manufactured in identical ways as compared to prosthetic valve 350. In one example, a pore size of the layer 383 is in the range of 2 to 20 μm, which is believed to result in a layer 383 that does not allow blood to flow through the layer 383 as most blood cells are around 10 microns. It is envisioned that some blood may pass but, due to active clotting, this would only occur for approximately 1-30 minutes, which is generally tolerated for most transcatheter prosthetic valves.

Figure 11C:
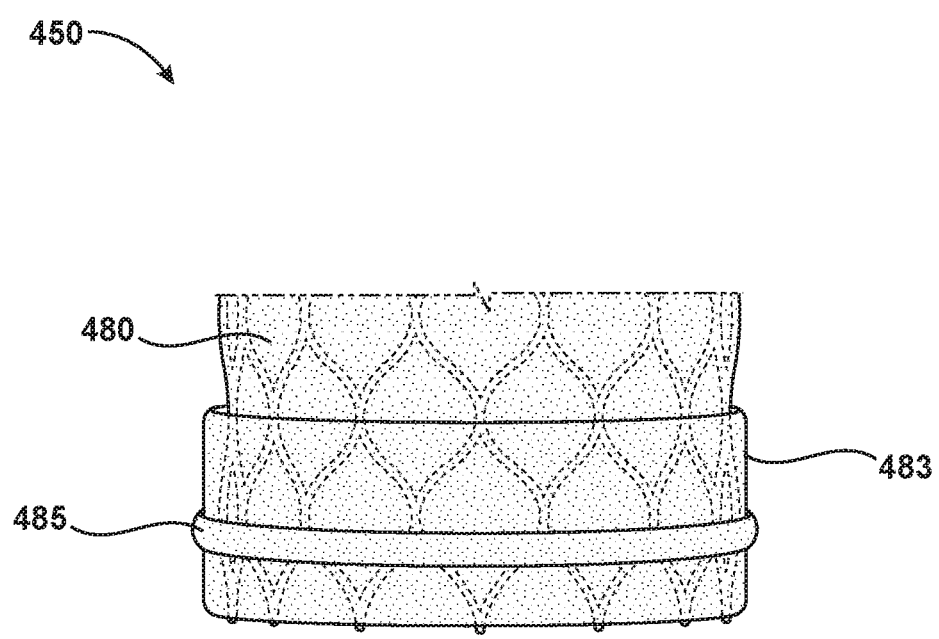
FIG. 11C depicts a partial, front illustration of an alternate second layer including an anti-PVL layer having a corrugated configuration.
Figure 11D:
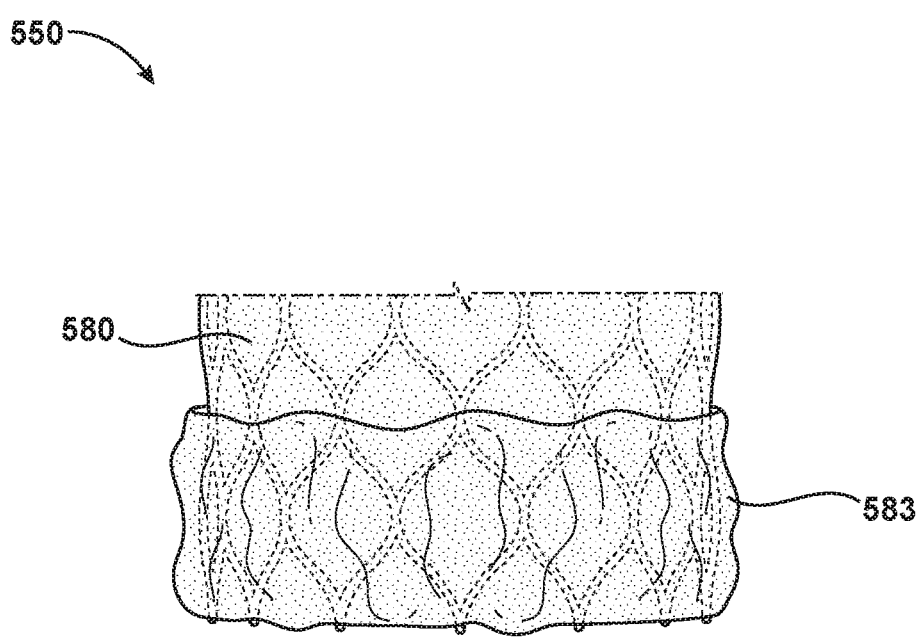
FIG. 11D depicts a partial, front illustration of an alternate second layer including an anti-PVL layer having a parachute configuration.
Figure 11E:
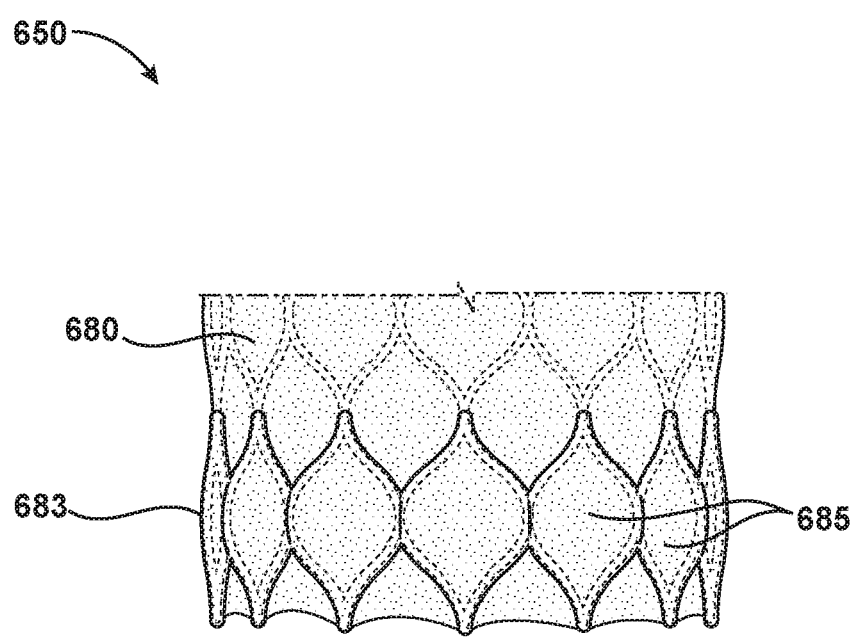
FIG. 11E depicts a partial, front illustration of an alternate second layer including an anti-PVL layer having a puffy configuration.

The anti-PVL layer 383 can be spun to have a variety of configurations. FIG. 11C depicts a prosthetic valve 450 including an alternate second layer 480 having a layer or area of increased thickness 483 having a corrugated configuration including one or more ridges 485. FIG. 11D depicts a prosthetic valve 550 including an alternate second layer 580 having a layer or area of increased thickness 483 having a parachute configuration. FIG. 11E depicts a prosthetic valve 650 including an alternate second layer 680 having a layer or area of increased thickness 683 having a puffy configuration in which a plurality of sections 685 extend outwardly with respect to cells of the stent frame. It is noted that prosthetic valves 450, 550, 650 can otherwise be similarly configured and manufactured in any of the ways disclosed herein with respect to other embodiments.

For example, the layer 383 can be spun to include a plurality of pleats or can be a parachute style layer, for example. In some embodiments, the layer of increased thickness 383 is made of the same material as other electrospun components of the prosthetic valve 350 (e.g., second layer 380). Alternatively, the layer of increased thickness 383 can be made of a different material. The layer of increased thickness 383 can be made of a biodegradable material such polycaprolactone or polylactic acid (PLLA) or their copolymers. The layer 383 also be made of bio-stable polymers such as polyurethane or the like. One advantage of prosthetic valves having the anti-PVL layer 383 is that the anti-PVL layer 383 can be directly electrospun on the outer surface of the frame 378 without having to use a tedious suturing process. Another advantage of the electrospun anti-PVL layer 383 is the microporous structure of the layer 383, which will promote tissue growth around the layer 383 to provide permanent and durable seal.

EXAMPLE 2.4 g of Tecoflex™ 80A polyurethane was dissolved in 1.76 g of dimethyl formamide and 15.8 g of chloroform. The solution was loaded onto a 10 mL syringe and delivery at speed of 6 mL/h. A NITINOL stent frame was loaded onto a 2.5 cm mandrel rotated at 1500 rpm. The height of the 1 8G needle and the stent frame was about 7 cm. The applied voltage was 8.51 kv. After 10 minutes of electrospinning a thin layer of the fabric material was deposited on the stent frame. The stent frame was crimped two times and the fabric material showed good adhesion to the stent frame.

With the second layer 380 formed on the first layer 376 and the frame 378, the motor 209 of the collection assembly 203 is disengaged in a next step 126 to stop rotation of the prosthetic valve mold 207. At this point in the method 100, the electrospun prosthetic valve 350 may be removed from the valve mold 207 in a step 128. As explained above, use of the valve mold 407 with separable segments 442 and mold base 440 makes this step easier. However, non-separable valve molds 207 and 507 may also be used. At this step in the method 100, the second layer 380 is disposed over the frame 378 and the first layer 376, and the frame 378 is disposed over, or more precisely circumferentially around the first layer 376 of the electrospun prosthetic valve 350 as illustrated in FIG. 11A.

At this point in the method 100, the electrospun prosthetic valve 350 may proceed to the step 134 of further processing the electrospun prosthetic valve 350, as will be described in more detail below. However, in some embodiments of the method 100, it may desirable to ensure that the first and second layers 376, 378 are sufficiently adhered to each other and to frame 378 such that delamination of the layers does not occur. Thus, optionally, further bonding of the first and second layers 376, 378 and the frame 378 may be performed.

Figure 12:
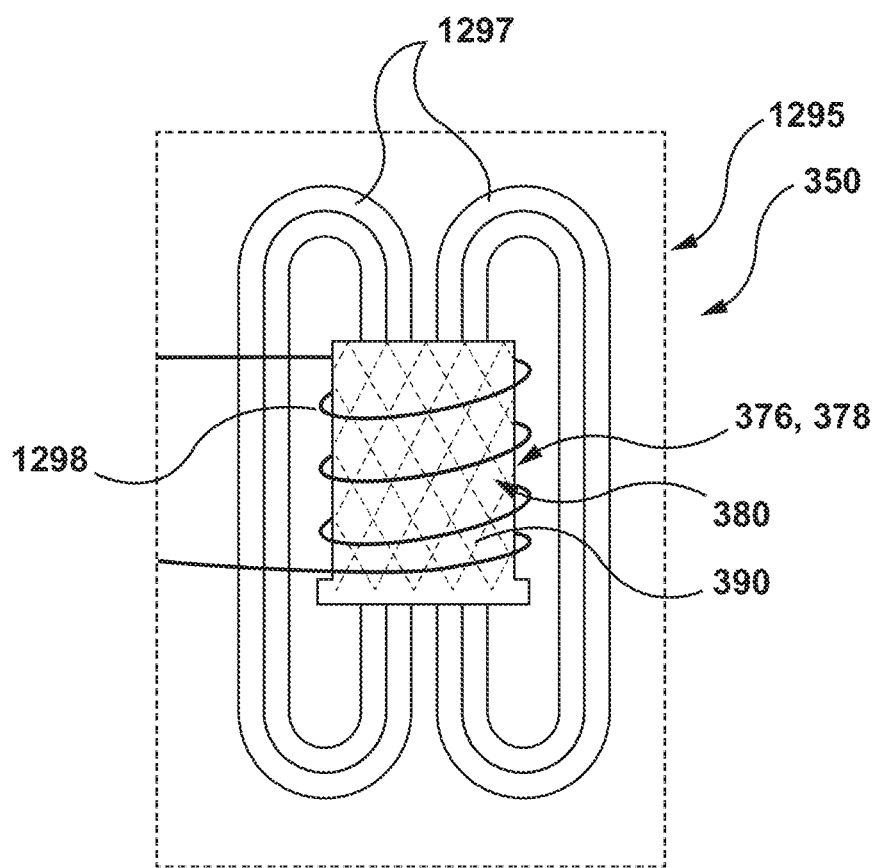
FIG. 12 depicts a step in the method of FIG. 1, wherein the second layer is coupled to the first layer by induction heating according to an embodiment hereof.

FIG. 12 illustrates a particular embodiment of an optional step 130 in the embodiment of the method 100 to further couple, bond, or adhere the first and second layers 376, 380 and the frame 378. In the embodiment of step 130 shown in FIG. 12, the frame 378 is heated with an induction heater 1295. As used herein, "induction heater" is used to describe a system configured to heat an electrically conducting object (i.e. the frame 378) by magnetic induction through heat generated in the object by eddy currents. More specifically, the electrospun prosthetic valve 350, including the first layer 376, the frame 378, and the second layer 380, is placed within a magnetic field 1297 generated by a coil 1298 of the induction heater 1295. The induction heater 1295 heats the frame 378 to a desired temperature to permit melting of the first and second layers 376, 380, respectively, in areas adjacent to the struts 390 of the frame 378. The induction heater 1295 is controlled to heat the frame 378 to a temperature just above the melting point of the first and second layers 376, 380. For example, and not by way of limitation, the frame 378 is heated to a temperature in a range of 60° to 160° Celsius. When the frame 378 is heated to a temperature above the melting temperature of the first and second layers 376, 380, the first and second layers 376, 380 melt or flow adjacent the struts 390 of the frame 378.

When the first and second layers 376, 380 have melted adjacent the struts 390 of the frame 378, in a next step 132 the induction heater 1295 is turned off and the first layer 376, the frame 378, and the second layer 380 are removed from the induction heater 1295. Once removed from the induction heater 1295, the frame 378 cools, and melted portions of the first and second layers 376, 380 adjacent the struts 390 of the frame 378 cool and congeal to further bond the first and second layers 376, 380 to each other and around the struts 390 of the frame 378. The coupling of the first layer 376 and the second layer 380 provides improved inter-layer strength between the first layer 376 and the second layer 380. The improved inter-layer strength prevents delamination of the first and second layers 376, 380 of the electrospun prosthetic valve 350. Because the induction heating heats the struts 390 of the frame 378, areas of the first and second layers 376, 380 spaced from the struts 390 in the cells do not melt. Thus, the limited melt area adjacent the struts 390 of the frame 378 does not sacrifice the overall porous structure of the first and second layers 376, 380 that promote tissue ingrowth in situ.

Although the induction heater 1295 has been described herein to thermally improve adhesion between the first and second layers 376, 380, in an alternative embodiment, adhesion between the first and second layers 376, 380 can be improved using other thermal sources. For example, and not by way of limitation, a laser or other suitable thermal device can be utilized. Further, a coupling or adhesion promoter can be utilized on the frame 378 to promote coupling of the first and/or second layers 376, 380 with the frame 378 and prevent delamination. In one example, the adhesion promoter is a vapor deposited poly(p-xylylene) ("parylene") polymer. Parylene is vapor deposited to covalently bonded to the frame. Other polymers or molecules can then be covalently bonded to the parylene adhesion promoter. In this way, the adhesion promoter creates a bridge for functional material to adhere to the metal frame. It is believed that a parylene adhesion promoter provides a stronger, more robust adhesion to the frame.

In a next step 134, further processing is performed to finalize the electrospun prosthetic valve 350. For example, and not by way of limitation, the further processing may include, but is not limited to, removal of excess material, such as a base portion 381 (shown in FIG. 11A) and separation of the leaflets 358, 360, 362. In an embodiment, a laser cutter (not shown) may be used to remove excess material and to separate the leaflets 358, 360, 362. In a particular embodiment wherein the valve mold 207 includes channels 244 described above, the laser or other cutter may cut along the corresponding channels formed in the prosthetic valve 350 to separate the leaflets 358, 360, 362 from each other.

Figure 13:
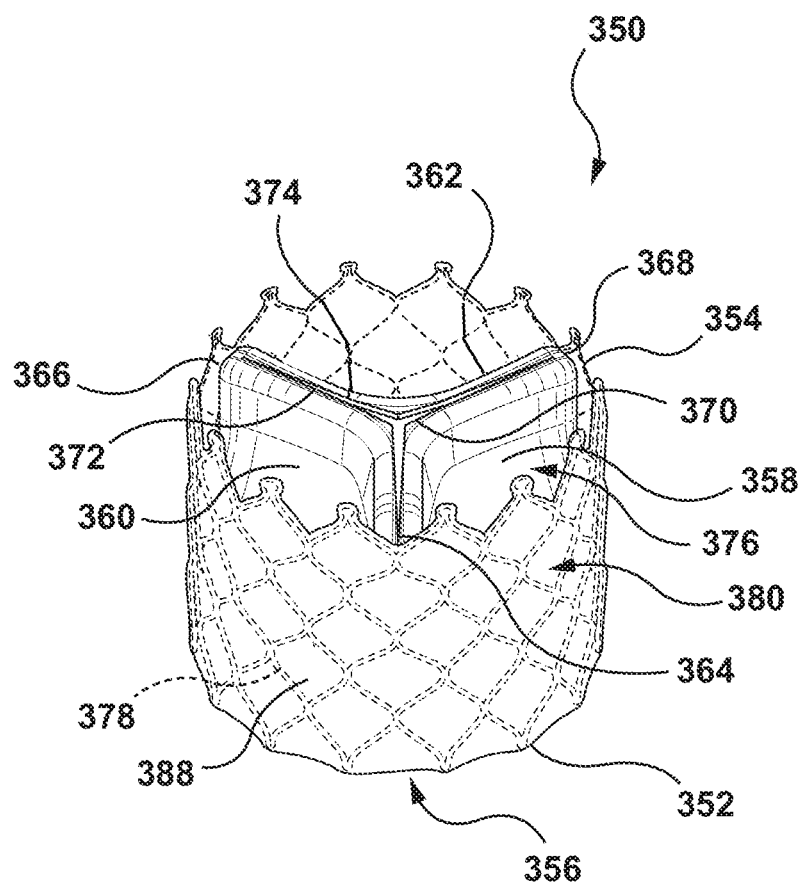
FIG. 13 depicts the electrospun prosthetic valve after further processing.

The finalized electrospun prosthetic valve 350 is shown in FIG. 13. The electrospun prosthetic valve 350 includes the inflow end 352, the outflow end 354 opposite the inflow end 352, and a lumen 356 extending from the inflow end 352 to the outflow end 354. The electrospun prosthetic valve 350 further includes a radially collapsed configuration for delivery, and a radially expanded configuration when deployed as shown in FIG. 13. In an embodiment, the prosthetic valve 350 is configured as a prosthetic heart valve configured to replace a damaged or diseased native heart valve. In an embodiment, the prosthetic valve 350 is self-expanding to return to the radially expanded configuration from the radially compressed configuration. In the embodiment of FIG. 13, the three (3) leaflets 358, 360, and 362 are formed adjacent the outflow end 354 of the electrospun prosthetic valve 350. Adjoining pairs of leaflets are attached to one another at their lateral ends to form commissures 364, 366, 368, with free edges 370, 372, 374 of the leaflets forming coaptation edges. The leaflets 358, 360, 362 are configured to permit flow in one direction, from the inflow end 352 to the outflow end 354 to regulate flow through the lumen 356 of the electrospun prosthetic valve 350. While the electrospun prosthetic valve 350 has been described as self-expanding, alternatively the electrospun prosthetic valve 350 can be balloon expandable.

As explained above, the electrospun prosthetic valve 350 includes the first or valve layer 376, the second or skirt layer 380, and the frame 378 disposed between the first and second layers 376, 380. The second layer 380 is configured to act as a paravalvular leakage (PVL) skirt permitting a tight seal with surrounding tissue when the electrospun prosthetic valve 350 is in the radially expanded configuration and deployed at a desired treatment location. Use of the second layer 380 as the paravalvular leakage (PVL) skirt reduces or eliminates the need for suturing the valve layer 376 to the frame 378.

While the electrospun prosthetic valve 350 is described herein and illustrated in FIG. 13 with the first layer 376, the second layer 380, and the frame 378, and further with the frame 378 disposed between the first and second layers 376, 380, this is by way of example and not limitation. In alternative embodiments hereof, the electrospun prosthetic valve 350 may include the first layer 376, the frame 378, and/or the second layer 380 in any combination, and may include more or fewer layers. Further, while the electrospun prosthetic valve 350 is described herein with three (3) leaflets 358, 360, 362, this too is by way of example and not limitation, and more or fewer leaflets may be formed with embodiments of electrospun prosthetic valves described herein.

Figure 14:
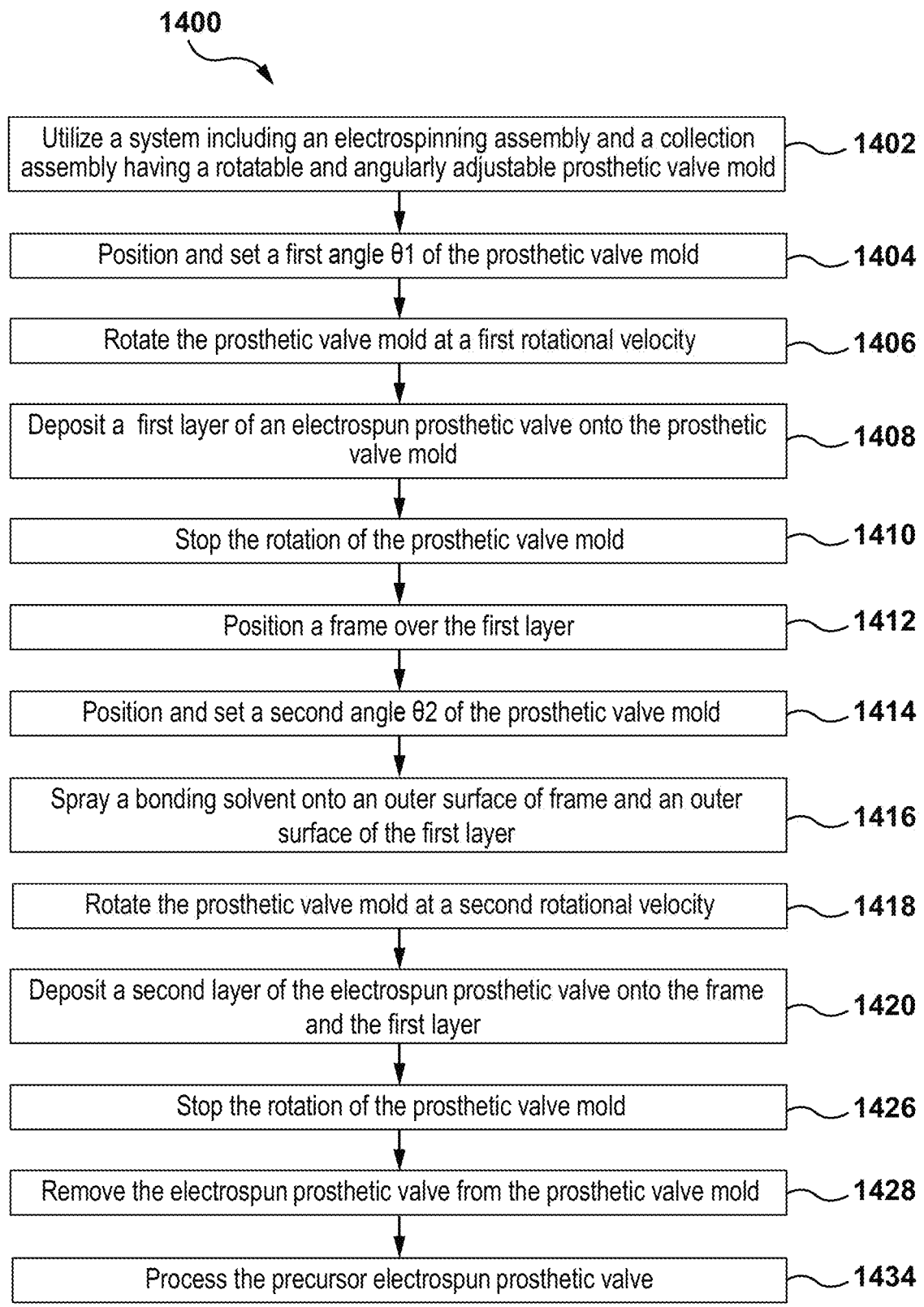
FIG. 14 depicts a flow chart showing steps in a method of making an electrospun prosthetic valve according to another embodiment hereof.

FIG. 14 is a flow chart showing a method 1400 of making a medical device such as an electrospun prosthetic valve 1550 according to another embodiment hereof. The method 1400 is similar to the method 100 of FIG. 1 except that steps to couple a first layer 1876 to a second layer 1880 of the electrospun prosthetic valve 1550 are different. Thus, the steps 1402, 1404, 1406, 1408, 1410, 1412, and 1414 of the method 1400 of FIG. 14 are similar to the steps 102, 104, 106, 108, 110, 112, and 114 previously described with respect to the method 100 of FIG. 1. Therefore, detailed descriptions of the steps 1402, 1404, 1406, 1408, 1410, 1412, and 1414 of the method 1400 will not be repeated here, and the description above regarding the method 100 and the electrospun prosthetic valve 350 applies to and is incorporated to the method 1400 and the electrospun prosthetic valve 1850. Thus, the electrospun prosthetic valve 1550 includes a first or valve layer 1576, a second or skirt layer 1580, and a frame 1578 disposed between the first layer 1576 and the second layer 1580. The various details and alternatives described above with respect to FIGS. 1-13 apply equally to the method 1400 and the electrospun prosthetic valve 1550.

Figure 15:
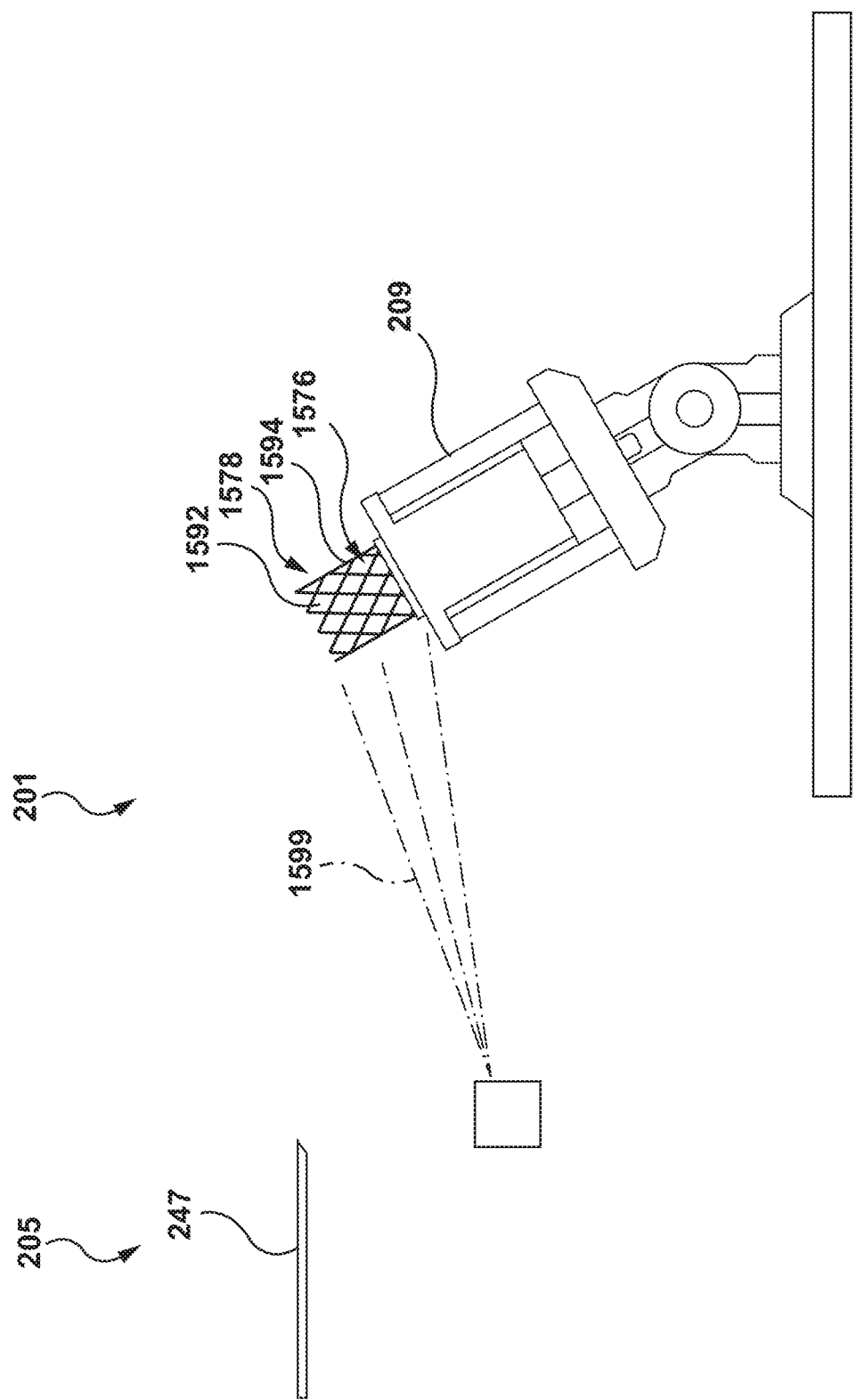
FIG. 15 depicts a step in the method of FIG. 14, wherein a bonding solvent is applied to an outer surface of a first layer and a frame of an electrospun prosthetic valve according to an embodiment hereof.

Accordingly, after the frame 1578 has been properly positioned about the first layer 1576 at the conclusion of the step 1412 and the second angle □2, has been set, in a next step 1416 a bonding solvent 1599 (and/or other adhesion promoter as disclosed herein) is applied to an outer surface 1592 of the first layer 1576 and an outer surface 1594 of the frame 1578, an illustrated example of which is illustrated in FIG. 15. The bonding solvent 1599 is configured to control or increase the tackiness of the first layer 1576 to couple, bond or adhere the second layer 1580 to the first layer 1576 when the second layer 1580 (illustrated in FIG. 16) is collected or distributed thereon as described below. Stated another way, the bonding solvent 1599 is configured to increase adhesion between the first and second layers 1576, 1580. More specifically, application of the bonding solvent 1599 wets and thereby increases the tackiness of the first layer 1576 such that when the second layer 1580 is distributed or collected thereon, the second layer 1580 and the first layer 1576 can flow to thereby couple to one another across the entirety of the first and second layers 1576, 1580. The bonding solvent 1599 can be any suitable solvent including, but not limited to chloroform, dimethylformamide (DMF) or acetic acid. The bonding solvent 1599 can be the same solvent utilized in the polymer solution 251, or can be of a lower volatility than the solvent utilized in the polymer solution 251. Further, the bonding solvent 1599 can be of a diluted, low viscosity formulation of the polymer solution 251 to further promote adhesion between the first layer 1576 and the second layer 1580 as described below. For example, and not by way of limitation, the bonding solvent 1599 can be 2% polymer by weight. Alternatively, an adhesive such as, but not limited to octyl-cyanoacrylate (OCA), or liquid silicone can be utilized in place of the bonding solvent 1599.

The bonding solvent 1599 can be applied to the outer surface 1592 of the first layer 1576 and the outer surface 1594 of the frame 1578 by various techniques, non-limiting examples of which include an atomizer, an airbrush, a sonic sprayer, vapor activation, electrospray or any other suitable application technique. In the embodiment of FIG. 15, the bonding solvent 1599 is sprayed onto the first layer 1576 and the frame 1578 with a sonic sprayer 1589. "Sonic sprayer" as used herein is intended to describe a spray process wherein ultrasonic sensors are utilized to spray precise amounts of a material (i.e. the bonding solvent 1599) onto the first layer 1576 and the frame 1578 to control the tackiness of the of the first layer 1576. Alternatively, the bonding solvent 1599 can be applied only to the outer surface 1592 of the first layer 1594.

When the bonding solvent 1599 has been distributed onto the first layer 1576 and the frame 1578, the motor 209 is engaged in a next step 1418. The motor 209 rotates the prosthetic valve mold 207, including the first layer 1576 and the frame 1578, in a first direction illustrated by the arrow 1682 in FIG. 16, at a desired second rotational velocity RV2. The second rotational velocity RV2 is selected to enable the even distribution of a second plurality of electrospun fibers 263B onto the outer surface 1592 of the first layer 1576 and the outer surface 1594 of the frame 1578, as previously described with reference to the step 106 and FIG. 6.

Figure 16:
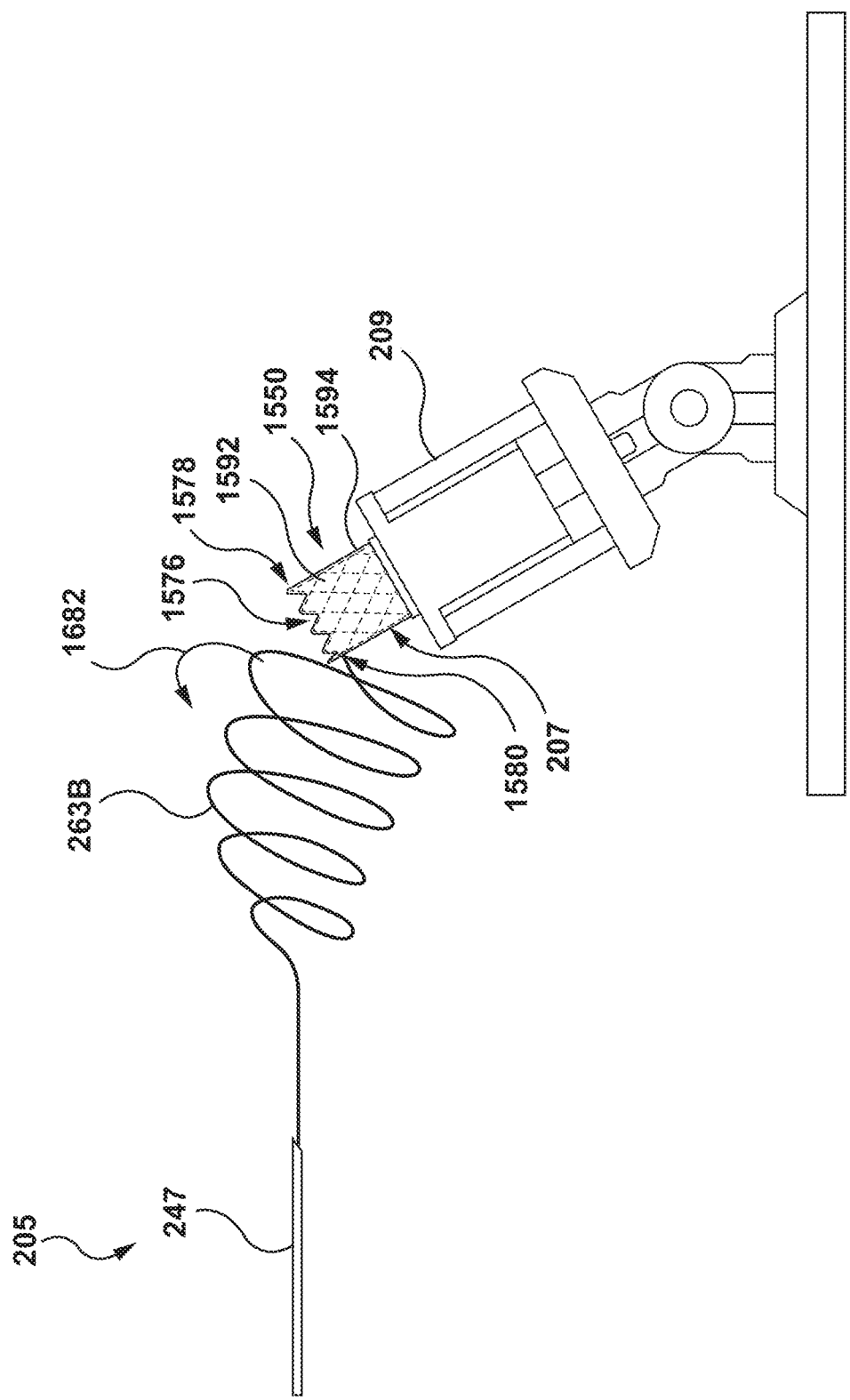
FIG. 16 depicts a step in the method of FIG. 14, wherein a second layer of a second plurality of electrospun fibers are deposited on an outer surface of the frame and the outer surface of the first layer.

In a next step 1420 illustrated in FIG. 16, with the prosthetic valve mold 207, including the first layer 1576 and the frame 1578 is positioned and rotating as desired, the electrospinning assembly 205 is engaged and the second layer 1580 is collected and distributed on the rotating outer surfaces 1592, 1594 of the first layer 1576 and the frame 1578, respectively. As the second layer 1580 is distributed onto the first layer 1576, the tackiness of the first layer 1576 permits the second layer 1580 to flow and to couple with the first layer 1576.

Figure 17:
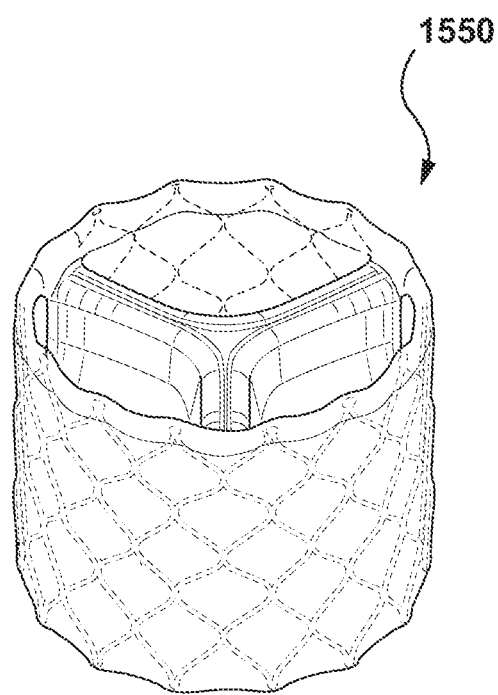
FIG. 17 depicts a perspective illustration of an electrospun prosthetic valve formed with the method of FIG. 14.
Figure 18:
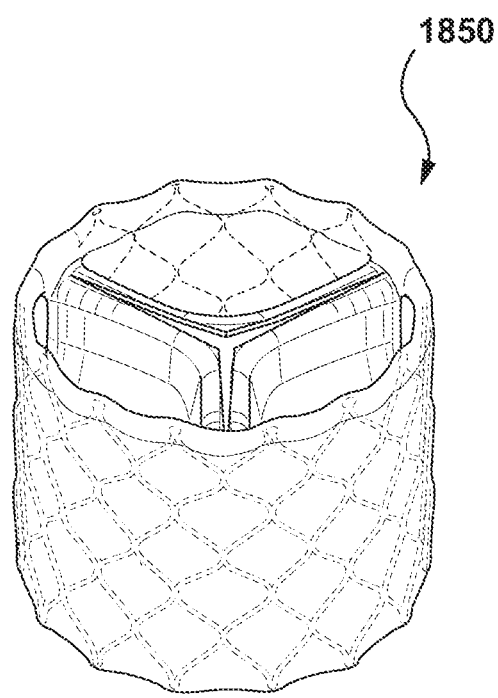
FIG. 18 depicts the electrospun prosthetic valve after further processing.

With the second layer 1580 distributed onto the first layer 1576 and the frame 1578, the motor 209 of the collection assembly 203 is disengaged in a next step 1426, the steps 1426, 1428, and 1434 are similar to the steps 126, 128, and 134 described above with respect to FIG. 1. Therefore, the details and variations will not be repeated herein and are incorporated into the method of FIG. 14. The electrospun prosthetic valve 1450 after step 1428 and prior to step 1434 is shown in FIG. 16. The electrospun prosthetic valve 1450 after step 1434 is shown in FIG. 17. As can be seen, at least the leaflets of the electrospun prosthetic valve 1450 have been separated, as described above with respect to the step 134 of the method 100.

Figure 19:
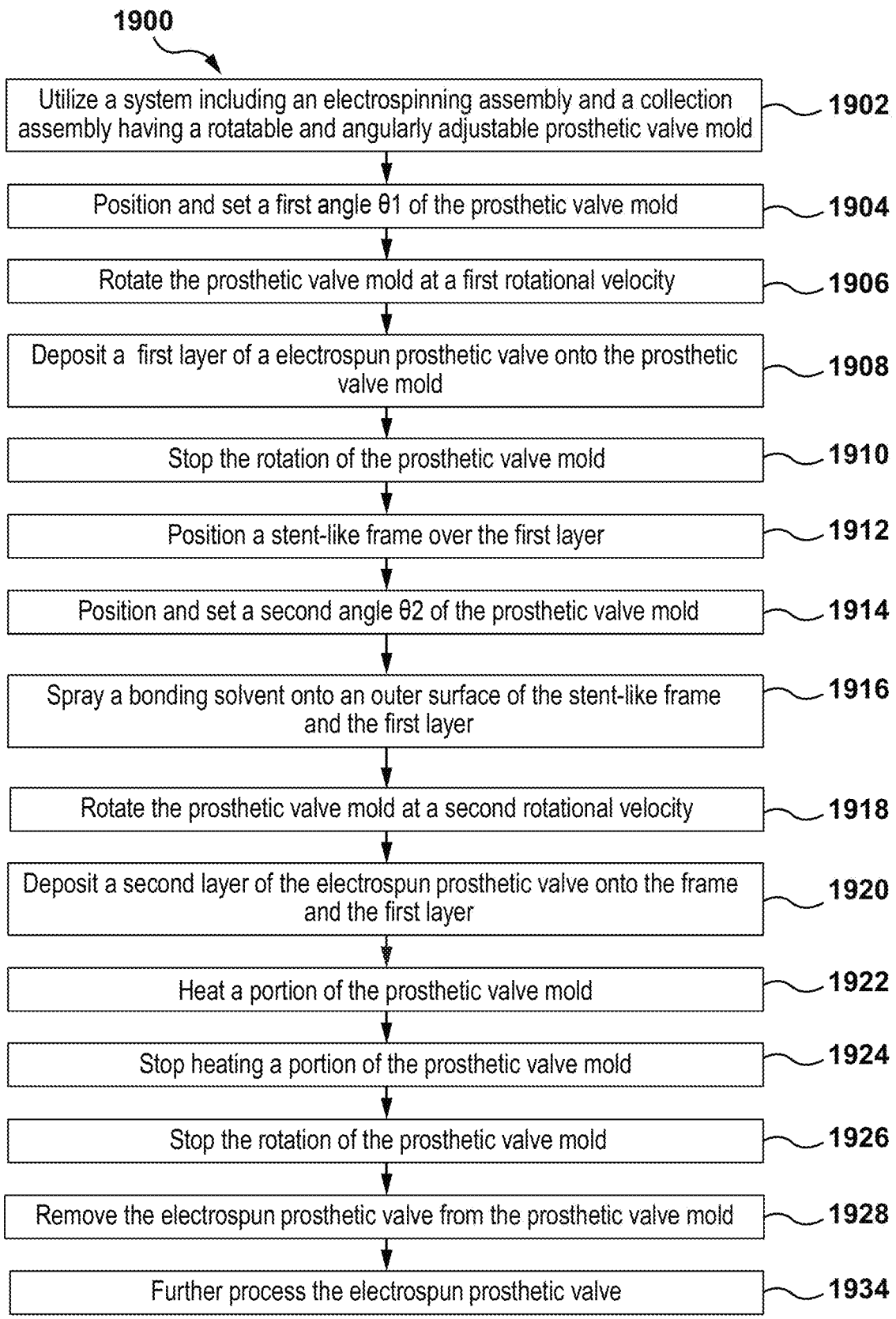
FIG. 19 depicts a flow chart showing steps in a method of making an electrospun prosthetic valve according to another embodiment hereof.
Figure 21:
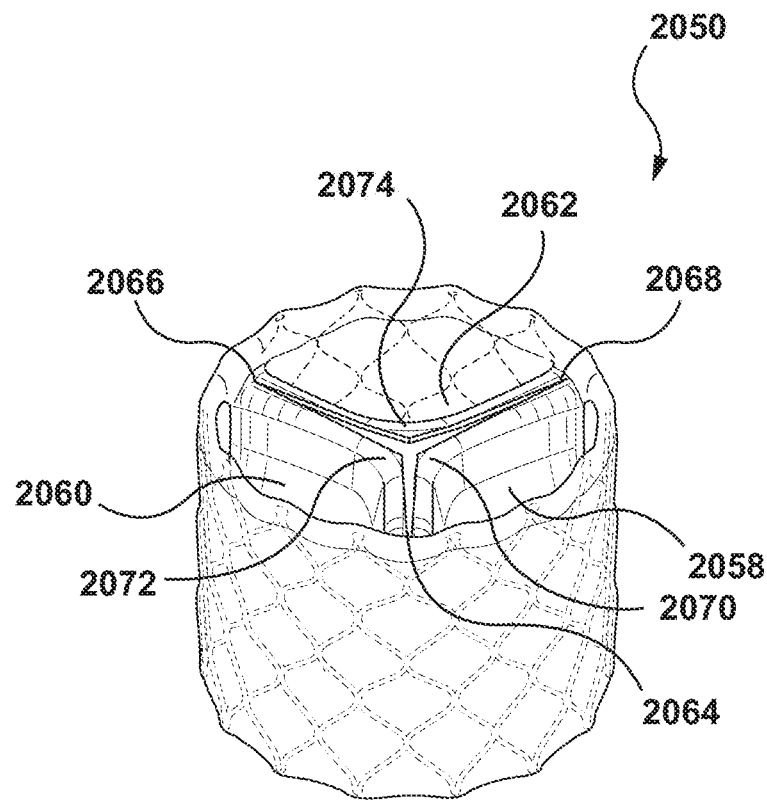
FIG. 21 depicts the electrospun prosthetic valve after further processing.

FIG. 19 is a flow chart showing a method 1900 of making a medical device such as an electrospun prosthetic valve 2050 of FIG. 21. Steps 1902, 1904, 1906, 1908, 1910, 1912, 1914, 1916, 1918, 1920, 1926, 1928 and 1934 of the method 1900 of FIG. 19 are similar to the steps 1402, 1404, 1406, 1408, 1410, 1412, 1414, 1416, 1418, 1420, 1426, 1428 and 1434 previously described with respect to the method 1400 of FIG. 14. Therefore, detailed descriptions of the steps 1902, 1904, 1906, 1908, 1910, 1912, 1914, 1916, 1918, 1920, 1926, 1928, and 1934 will not be repeated here. Accordingly, the electrospun prosthetic valve 2050 is formed in an electrospinning process and then processed in step 1934. However, the method 1900 of FIG. 19 includes the additional steps 1922 and 1924 to improve structural strength of selected portions 2083 of the electrospun prosthetic valve 2050.

Figure 20:
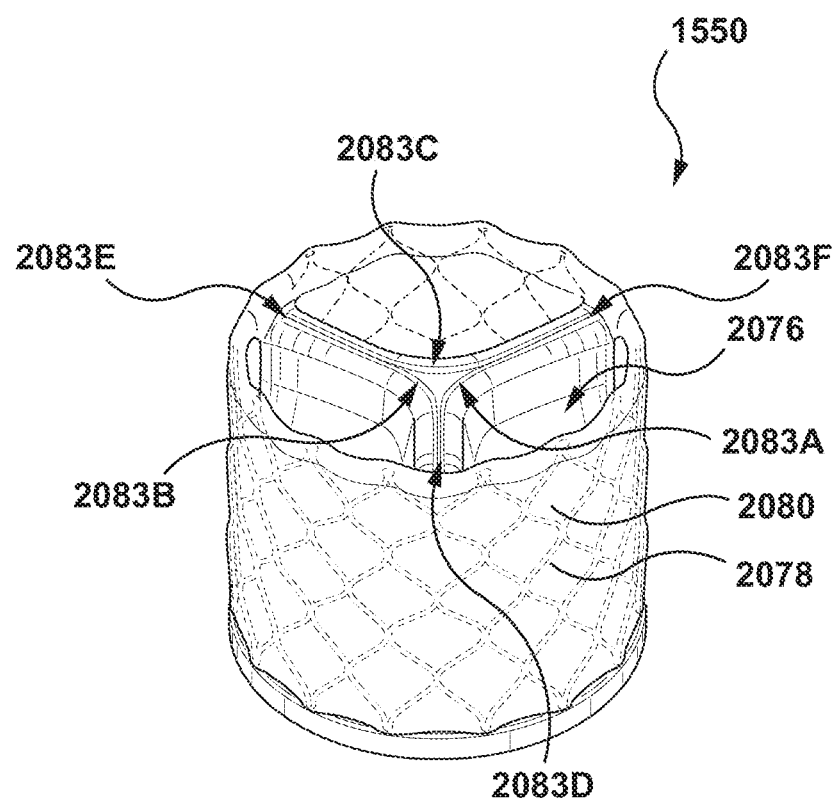
FIG. 20 depicts a step in the method of FIG. 19, wherein selected portions of a precursor electrospun prosthetic valve are crystalized.

Picking up after the step 1920, in a next step 1922, with a second layer 2080 disposed on a frame 2078 and a first layer 2076 of the electrospun prosthetic valve 2050, the heated portions 546 (FIG. 3C) of the prosthetic valve mold 507 (FIG. 3C) are heated to melt corresponding selected portions 2083A, 2083B, 2083C, 2083D, 2083E, and 2083F (collectively referred to herein as "selected portions 2083") of the first and second layer 2076, 2080. The temperature of the first portions 546 of the prosthetic valve mold 507 is precisely controlled to melt the first and second layers 2076, 2080 in the selected portions 2083 only. Once melted, in a next step 1924 the first portions 246 of the prosthetic valve mold 507 are cooled to crystalize the selected portions 2083 of the electrospun prosthetic valve 2050 to improve the strength in the electrospun prosthetic valve 2050 in the crystalized selected portions 2083. Although the steps 1922 and 1924 are discussed above as occurring after the second layer 2080 is deposited on the first layer 2076 and the frame 2078, the step 1922 may be performed simultaneously with the step 1920 of depositing the second layer 2080 on the first layer 2076 and the frame 2078. Thus, as the second layer 2080 is being deposited, the heated portions 546 of the valve mold 507 crystallize the first and second layers 2076, 2080 for improved strength in these areas. The steps 1926, 1928, and 1934 are then performed to form the electrospun prosthetic valve 2050 shown in FIG. 20 (prior to step 1934) and FIG. 21 (after step 1934).

In the embodiment of the electrospun prosthetic valve 2050 of FIG. 21, the free edges 2070, 2072, 2074 and the corresponding commissures 2064, 2066, 2068 of the leaflets 2058, 2060, and 2062 were heated and crystalized. Accordingly, the crystalized free edges 2170, 2172, 2174 and the corresponding commissures 2164, 2166, 2168 exhibit improved strength. However, crystallization reduces the porosity of the electrospun fibers 263 of the electrospun prosthetic valve 2050 in the crystallized areas, which negatively impacting tissue ingrowth. While it is desirable to maintain the porosity of the electrospun fibers throughout the prosthetic valve 2050 to promote tissue ingrowth, limited portions of the electrospun prosthetic valve 2050 can be sacrificed to improve the overall mechanical performance of the electrospun prosthetic valve 2050 to ensure physiological viability. Stated another way, selected portions of the electrospun prosthetic valve 2050 can be melted and then crystalized to provide improved structural strength in desired locations while minimizing loss of the overall porous structure of the electrospun prosthetic valve 2050 that promote tissue ingrowth in situ.

Although the steps 1922, 1924 have been described as improving the strength of the crystallized the free edges 2070, 2072, 2074 and the commissures 2064, 2066, 2068 of the leaflets 2058, 2060, 2062, of the electrospun prosthetic valve 2150, this too is by way of example and not limitation and in alternative embodiments, other portions of the electrospun prosthetic valve 2050 can be selectively melted and crystallized in any combination.

While various embodiments according to the present disclosure have been described above, it should be understood that they have been presented by way of illustration and example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A method of forming an electrospun prosthetic valve, the method comprising the steps of:
    angularly adjusting a prosthetic valve mold to a first angle, the valve mold coupled to a first portion of a bracket, and a base coupled to a second portion of the bracket such that angularly adjusting the prosthetic valve mold comprises angularly adjusting the first portion of the bracket relative to the second portion of the bracket, the bracket comprising a locking mechanism operable between an unlocked configuration and a locked configuration, wherein in the unlocked conguration, the first portion of the bracket is angularly adjustable relative to the second portion of the bracket about a pivot joint to change the first angle between the valve mold and the base within a range between 0 degrees to 180 degrees, and in the locked configuration, the first portion of the bracket is non-movable relative to the second portion of the bracket,
    rotating the prosthetic valve mold at a first rotational velocity;
    depositing a first layer of a first plurality of electrospun fibers onto the prosthetic valve mold;
    stopping the rotation of the prosthetic valve mold from the first rotational velocity;
    positioning a frame radially outward of the first layer;
    rotating the prosthetic valve mold including the first layer and the frame at a second rotational velocity;
    depositing a second layer of a second plurality of electrospun fibers onto an outer surface of the frame and an outer surface of the first layer;
    stopping the rotation of the prosthetic valve mold, and
    processing the precursor electrospun prosthetic valve to form the electrospun prosthetic valve.

2. The method of forming the electrospun prosthetic valve of claim 1, further including the step of angularly adjusting the prosthetic valve mold to a second angle after the step of stopping the rotation of the prosthetic valve mold from the first rotational velocity, and before rotating the prosthetic valve mold at a second rotational velocity.

3. The method of forming the electrospun prosthetic valve of claim 1, further including the step of coupling the second layer to the first layer with one of an induction heater or a bonding solvent.

4. The method of forming the electrospun prosthetic valve of claim 3, wherein a bonding solvent is applied to the outer surface of the first layer after the step of positioning the frame over the first layer of the prosthetic valve and before the step of depositing the second layer of the second plurality of electrospun fibers onto the frame and the first layer.

5. The method of forming the electrospun prosthetic valve of claim 1, wherein the step of depositing the second layer includes depositing electrospun fibers having an area of increased thickness with respect to other regions of the second layer, the area of increased thickness extending around a circumference of the frame such that the second layer comprises a non-uniform diameter along a length of the prosthetic valve with the area of increased thickness comprising a larger diameter than the other regions of the second layer.

6. The method of forming the electrospun prosthetic valve of claim 1, comprising vapor depositing parylene on the frame.

7. The method of forming the electrospun prosthetic valve of claim 1, wherein the prosthetic valve mold is rotatable in the range of 0-1,000 revolutions per minute.

8. The method of forming the electrospun prosthetic valve of claim 1, wherein the prosthetic valve mold extends along a first longitudinal axis, and a second longitudinal axis extends through the pivot point and parallel to a collection base, the first angle defined between the first longitudinal axis and the second longitudinal axis and adjustable within the range between 0 degrees to 180 degrees.

9. The method of forming the electrospun prosthetic valve of claim 1, wherein the angular adjustment of the prosthetic valve mold is configured to enable an even distribution of the first or the second pluralities of electrospun fibers during deposition thereon, further wherein the prosthetic valve mold is coupled to a motor that rotates the prosthetic valve mold at the first rotational velocity and the second rotational velocity, the motor coupled to the first portion of the bracket such that the motor and the valve mold are angularly adjusted relative to the base.

10. The method of forming the electrospun prosthetic valve of claim 1, further including the steps of heating a first portion of the prosthetic valve mold to melt a corresponding selected portion of the first and second layers of the electrospun prosthetic valve, and then cooling the electrospun prosthetic valve to crystalize and strengthen the selected portion of the precursor electrospun prosthetic valve prior to the step of processing the precursor electrospun prosthetic valve.

11. The method of forming the electrospun prosthetic valve of claim 10, wherein the first portion of the prosthetic valve mold is a plurality of first portions.

12. The method of claim 1, wherein the prosthetic valve mold comprises a plurality of segments removably attached to a mold base, the plurality of segments comprising stems that each project outwardly from leaflet portions of the plurality of segments, and wherein the stems are configured to be received within stem openings of the mold base, and wherein the plurality of segments are shaped to form a corresponding leaflet of the first layer of the first plurality of electrospun fibers.

13. A method of forming an electrospun prosthetic valve, the method comprising the steps of:
angularly adjusting a prosthetic valve mold to a first angle, the prosthetic valve mold extending between a first end and a second end, the second end coupled to a motor;
rotating the prosthetic valve mold at a first rotational velocity;
depositing a first layer of a first plurality of electrospun fibers onto the prosthetic valve mold such that the first layer covers the first end of the prosthetic valve mold, the prosthetic valve mold comprising a plurality of separate segments extending between a first end and a second end, with the second end of each of the plurality of separate segments comprising stems that project outwardly and are removably attached to a mold base and the first end comprising one or more channels, and wherein each segment of the plurality of segments is shaped to form a corresponding leaflet of the first layer of the first plurality of electrospun fibers and the one or more channels forms a corresponding channel of the first layer of the first plurality of electrospun fibers,
stopping the rotation of the prosthetic valve mold from the first rotational velocity;
positioning a frame radially outward of the first layer such that all of the first layer is received within a lumen of the frame that extends between an inflow end and an outflow end of the frame, the inflow end adjacent to the second end of the prosthetic valve mold;
rotating the prosthetic valve mold including the first layer and the frame at a second rotational velocity;
depositing a second layer of a second plurality of electrospun fibers onto an outer surface of the frame and an outer surface of the first layer;
stopping the rotation of the prosthetic valve mold, and
processing the precursor electrospun prosthetic valve to form the electrospun prosthetic valve.

* * * * *